United States Patent
Purcell et al.

(10) Patent No.: US 10,349,983 B2
(45) Date of Patent: *Jul. 16, 2019

(54) PIVOTAL BONE ANCHOR ASSEMBLY WITH BIASED BUSHING FOR PRE-LOCK FRICTION FIT

(71) Applicant: Alphatec Spine, Inc., Carlsbad, CA (US)

(72) Inventors: Thomas Purcell, Solana Beach, CA (US); Don Hair, Moreno Valley, CA (US); Tamas T Frech, Sun City, CA (US)

(73) Assignee: Alphatec Spine, Inc., Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/163,797

(22) Filed: Jan. 24, 2014

(65) Prior Publication Data

US 2014/0142635 A1 May 22, 2014

Related U.S. Application Data

(63) Continuation of application No. 13/507,857, filed on Aug. 2, 2012, now Pat. No. 8,636,775, which is a
(Continued)

(51) Int. Cl.
*A61B 17/70* (2006.01)

(52) U.S. Cl.
CPC ...... *A61B 17/7037* (2013.01); *A61B 17/7038* (2013.01); *A61B 17/7032* (2013.01)

(58) Field of Classification Search
CPC ............ A61B 17/7037; A61B 17/7038; A61B 17/7032
(Continued)

(56) References Cited

U.S. PATENT DOCUMENTS

| 154,864 A | 9/1874 | Harvey |
| 791,548 A | 6/1905 | Fischer |

(Continued)

FOREIGN PATENT DOCUMENTS

| AU | 2012203959 | 8/2012 |
| DE | 373809 | 4/1923 |

(Continued)

OTHER PUBLICATIONS

Brochure of Tyco/Healthcare/Surgical Dynamics on Spiral Radius 90D, Publication Date: Sep. 2001, pp. 1-8.
(Continued)

*Primary Examiner* — Pedro Philogene
*Assistant Examiner* — David C Comstock
(74) *Attorney, Agent, or Firm* — Polsinelli PC

(57) ABSTRACT

A spinal screw assembly providing an adjustable securement of a fixation rod across at least two vertebrae. The assembly includes a pedicle screw having a spherical head portion, a threaded shaft portion and a tool engagement surface in the head portion for use in driving the screw into a vertebrae. The head portion of the screw is positioned in a body member adjacent a curvilinear surface disposed about an aperture in the end of the body member such that the shaft portion of the screw extends therethrough and the curvilinear inner surface abuts and mates with the head portion of the screw so as to define a ball joint therewith. The body member additionally defines a pair of opposed parallel slots therein adapted to receive a portion of the fixation rod and a locking cap bears against the fixation rod to releasably secure the rod within the assembly.

30 Claims, 14 Drawing Sheets

Related U.S. Application Data continuation of application No. 12/154,448, filed on May 23, 2008, now Pat. No. 8,298,265, which is a continuation of application No. 10/848,946, filed on May 19, 2004, now Pat. No. 7,377,923.

(60) Provisional application No. 60/472,578, filed on May 22, 2003, provisional application No. 60/527,060, filed on Dec. 4, 2003.

(58) Field of Classification Search
USPC .............. 606/246, 264–272, 301, 305, 308; 411/393; 403/76, 77, 83, 84, 90, 362
See application file for complete search history.

(56) References Cited

U.S. PATENT DOCUMENTS

| | | |
|---|---|---|
| 1,300,275 A | 4/1919 | Johnson |
| 1,330,673 A | 2/1920 | Anderson |
| 1,472,464 A | 10/1923 | Ellison |
| 2,083,092 A | 6/1937 | Richer |
| 2,201,087 A | 5/1940 | Hallowell |
| 2,239,352 A | 4/1941 | Cherry |
| 2,243,717 A | 5/1941 | Moreira |
| 2,295,314 A | 9/1942 | Whitney |
| 2,346,346 A | 4/1944 | Anderson |
| 2,362,999 A | 11/1944 | Elmer |
| 2,445,978 A | 7/1948 | Stellin |
| 2,531,892 A | 11/1950 | Reese |
| 2,532,815 A | 12/1950 | Kindsvatter et al. |
| 2,537,029 A | 1/1951 | Cambern |
| 2,553,337 A | 5/1951 | Shafer |
| 2,778,265 A | 1/1957 | Brown |
| 2,813,450 A | 11/1957 | Dzus |
| 2,877,681 A | 3/1959 | Brown |
| 2,927,332 A | 3/1960 | Moore |
| 2,969,250 A | 1/1961 | Kull |
| 3,013,244 A | 12/1961 | Rudy |
| 3,143,029 A | 8/1964 | Brown |
| D200,217 S | 2/1965 | Curtiss |
| 3,236,275 A | 2/1966 | Smith |
| 3,370,341 A | 2/1968 | Allsop |
| 3,444,775 A | 5/1969 | Hills |
| 3,498,174 A | 3/1970 | Schuster et al. |
| 3,584,667 A | 6/1971 | Reiland |
| 3,604,487 A | 9/1971 | Gilbert |
| 3,640,416 A | 2/1972 | Temple |
| 3,812,757 A | 5/1974 | Reiland |
| 3,963,322 A | 6/1976 | Gryctko |
| 3,989,284 A | 11/1976 | Blose |
| 3,997,138 A | 12/1976 | Crock et al. |
| 4,013,071 A | 3/1977 | Rosenberg |
| 4,033,139 A | 7/1977 | Frederick |
| 4,041,939 A | 8/1977 | Hall |
| 4,103,422 A | 8/1978 | Weiss et al. |
| 4,190,091 A | 2/1980 | Colognori |
| 4,269,246 A | 5/1981 | Larson et al. |
| 4,347,845 A | 9/1982 | Mayfield |
| 4,369,769 A | 1/1983 | Edwards |
| 4,373,754 A | 2/1983 | Bollfrass et al. |
| 4,409,968 A | 10/1983 | Drummond |
| 4,448,191 A | 5/1984 | Rodnyansky et al. |
| 4,484,570 A | 11/1984 | Sutter et al. |
| 4,492,500 A | 1/1985 | Ewing |
| 4,506,917 A | 3/1985 | Hansen |
| 4,577,448 A | 3/1986 | Howorth |
| 4,600,224 A | 7/1986 | Blose |
| 4,600,225 A | 7/1986 | Blose |
| 4,641,636 A | 2/1987 | Cotrel |
| 4,653,481 A | 3/1987 | Howland et al. |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,763,644 A | 8/1988 | Webb |
| 4,764,068 A | 8/1988 | Crispell |
| 4,790,297 A | 12/1988 | Luque |
| 4,805,602 A | 2/1989 | Puno et al. |
| 4,815,453 A | 3/1989 | Cotrel |
| 4,836,196 A | 6/1989 | Park et al. |
| 4,838,264 A | 6/1989 | Bremer et al. |
| 4,850,775 A | 7/1989 | Lee et al. |
| 4,877,020 A | 10/1989 | Vich |
| 4,887,596 A | 12/1989 | Sherman |
| 4,917,606 A | 4/1990 | Miller |
| 4,946,458 A | 8/1990 | Harms et al. |
| 4,950,269 A | 8/1990 | Gaines, Jr. |
| 4,961,740 A | 10/1990 | Ray et al. |
| 5,005,562 A | 4/1991 | Cotrel |
| 5,019,080 A | 5/1991 | Hemer |
| 5,022,791 A | 6/1991 | Isler |
| 5,034,011 A | 7/1991 | Howland |
| 5,042,982 A | 8/1991 | Harms et al. |
| 5,056,492 A | 10/1991 | Banse |
| 5,067,428 A | 11/1991 | Dickerson et al. |
| 5,067,955 A | 11/1991 | Cotrel |
| 5,073,074 A | 12/1991 | Corrigan et al. |
| 5,084,048 A | 1/1992 | Jacob et al. |
| 5,092,635 A | 3/1992 | DeLange et al. |
| 5,102,412 A | 4/1992 | Rogozinski |
| 5,129,388 A | 7/1992 | Vignaud et al. |
| 5,129,899 A | 7/1992 | Small et al. |
| 5,147,360 A | 9/1992 | Dubousset |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,679 A | 1/1993 | Lin |
| 5,176,680 A | 1/1993 | Vignaud et al. |
| 5,180,393 A | 1/1993 | Commarmond |
| 5,201,734 A | 4/1993 | Cozad et al. |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,263,953 A | 11/1993 | Bagby |
| 5,275,601 A | 1/1994 | Gogolewski et al. |
| 5,282,707 A | 2/1994 | Palm |
| 5,282,862 A | 2/1994 | Barker et al. |
| 5,282,863 A | 2/1994 | Burton |
| 5,306,275 A | 4/1994 | Bryan |
| 5,312,404 A | 5/1994 | Asher et al. |
| 5,321,901 A | 6/1994 | Kelly |
| 5,330,472 A | 7/1994 | Metz-Stavenhagen |
| 5,334,203 A | 8/1994 | Wagner |
| 5,346,493 A | 9/1994 | Stahurski et al. |
| 5,354,292 A | 10/1994 | Braeuer et al. |
| 5,354,299 A | 10/1994 | Coleman |
| 5,358,289 A | 10/1994 | Banker et al. |
| 5,360,431 A | 11/1994 | Puno et al. |
| 5,364,400 A | 11/1994 | Rego, Jr. et al. |
| 5,375,823 A | 12/1994 | Navas |
| 5,382,248 A | 1/1995 | Jacobson et al. |
| 5,385,583 A | 1/1995 | Cotrel |
| 5,387,211 A | 2/1995 | Saadatmanesh et al. |
| 5,387,212 A | 2/1995 | Yuan et al. |
| 5,395,371 A | 3/1995 | Miller et al. |
| 5,409,488 A | 4/1995 | Ulrich |
| 5,409,489 A | 4/1995 | Sioufi |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,434,001 A | 7/1995 | Yamada et al. |
| 5,443,467 A | 8/1995 | Biedermann et al. |
| 5,466,237 A | 11/1995 | Byrd, III et al. |
| 5,466,238 A | 11/1995 | Lin |
| 5,468,241 A | 11/1995 | Metz-Stavenhagen et al. |
| 5,474,551 A | 12/1995 | Finn et al. |
| 5,474,555 A | 12/1995 | Puno et al. |
| 5,476,462 A | 12/1995 | Allard et al. |
| 5,476,464 A | 12/1995 | Metz-Stavenhagen et al. |

(56) References Cited

U.S. PATENT DOCUMENTS

| | | |
|---|---|---|
| 5,480,401 A | 1/1996 | Navas |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,499,892 A | 3/1996 | Reed |
| 5,501,684 A | 3/1996 | Schlapfer et al. |
| 5,505,731 A | 4/1996 | Tornier |
| 5,507,745 A | 4/1996 | Logroscino et al. |
| 5,507,747 A | 4/1996 | Yuan et al. |
| 5,534,001 A | 7/1996 | Schlapfer et al. |
| 5,540,688 A | 7/1996 | Navas |
| 5,545,165 A | 8/1996 | Biedermann et al. |
| 5,549,607 A | 8/1996 | Olson et al. |
| 5,549,608 A | 8/1996 | Errico et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,578,033 A | 11/1996 | Errico et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,605,458 A | 2/1997 | Bailey et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,609,593 A | 3/1997 | Errico et al. |
| 5,609,594 A | 3/1997 | Errico et al. |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schaefer et al. |
| 5,647,873 A | 7/1997 | Errico et al. |
| 5,653,710 A | 8/1997 | Harle |
| 5,662,652 A | 9/1997 | Schaefer et al. |
| 5,662,653 A | 9/1997 | Songer et al. |
| 5,667,508 A | 9/1997 | Errico et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann |
| 5,676,665 A | 10/1997 | Bryan |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,683,391 A | 11/1997 | Boyd |
| 5,690,630 A | 11/1997 | Errico et al. |
| 5,702,393 A | 12/1997 | Pfaifer |
| 5,711,709 A | 1/1998 | McCoy |
| 5,713,705 A | 2/1998 | Grunbichler |
| 5,713,898 A | 2/1998 | Stuecker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,797,911 A | 8/1998 | Sherman et al. |
| 5,800,435 A | 9/1998 | Errico et al. |
| 5,800,547 A | 9/1998 | Schaefer et al. |
| 5,817,094 A | 10/1998 | Errico et al. |
| 5,863,293 A | 1/1999 | Richelsoph |
| 5,873,878 A | 2/1999 | Harms et al. |
| D407,302 S | 3/1999 | Lawson |
| 5,876,402 A | 3/1999 | Errico et al. |
| 5,879,351 A | 3/1999 | Viart |
| 5,882,350 A | 3/1999 | Ralph et al. |
| 5,902,303 A | 5/1999 | Eckhof et al. |
| RE36,221 E | 6/1999 | Breard et al. |
| 5,910,141 A | 6/1999 | Morrison et al. |
| 5,910,142 A | 6/1999 | Tatar |
| 5,928,236 A | 7/1999 | Augagneur et al. |
| 5,938,663 A | 8/1999 | Petreto |
| 5,941,880 A | 8/1999 | Errico et al. |
| 5,944,465 A | 8/1999 | Janitzki |
| 5,951,553 A | 9/1999 | Betz et al. |
| 5,961,517 A | 10/1999 | Biedermann et al. |
| 5,964,760 A | 10/1999 | Richelsoph |
| 5,964,767 A | 10/1999 | Tapia et al. |
| 5,997,539 A | 12/1999 | Errico et al. |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,078 A | 4/2000 | Parker |
| 6,056,753 A | 5/2000 | Jackson |
| 6,063,088 A | 5/2000 | Winslow |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,601 A | 9/2000 | Tatar |
| 6,117,137 A | 9/2000 | Halm et al. |
| 6,129,763 A | 10/2000 | Chauvin et al. |
| 6,132,431 A | 10/2000 | Nilsson et al. |
| 6,136,002 A | 10/2000 | Shih et al. |
| 6,136,003 A | 10/2000 | Hoeck et al. |
| 6,143,032 A | 11/2000 | Schaefer et al. |
| 6,146,383 A | 11/2000 | Studer et al. |
| 6,149,533 A | 11/2000 | Finn |
| 6,162,223 A | 12/2000 | Orsak et al. |
| 6,168,597 B1 | 1/2001 | Biedermann et al. |
| 6,183,472 B1 | 2/2001 | Lutz |
| 6,186,718 B1 | 2/2001 | Fogard |
| 6,193,719 B1 | 2/2001 | Gournay et al. |
| 6,193,720 B1 | 2/2001 | Yuan et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,235,028 B1 | 5/2001 | Brumfield et al. |
| 6,235,034 B1 | 5/2001 | Bray |
| 6,241,730 B1 | 6/2001 | Alby |
| 6,241,731 B1 | 6/2001 | Fiz |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,602 B1 | 7/2001 | Justis |
| 6,261,039 B1 | 7/2001 | Reed |
| 6,267,764 B1 | 7/2001 | Elberg |
| 6,267,765 B1 | 7/2001 | Taylor et al. |
| 6,280,445 B1 | 8/2001 | Morrison et al. |
| 6,287,308 B1 | 9/2001 | Betz et al. |
| 6,296,643 B1 | 10/2001 | Hopf et al. |
| 6,299,613 B1 | 10/2001 | Ogilvie et al. |
| 6,299,616 B1 | 10/2001 | Beger |
| 6,302,888 B1 | 10/2001 | Mellinger et al. |
| 6,309,391 B1 | 10/2001 | Crandall et al. |
| 6,315,564 B1 | 11/2001 | Levisman |
| 6,322,108 B1 | 11/2001 | Riesselmann et al. |
| RE37,665 E | 4/2002 | Ralph et al. |
| 6,368,321 B1 | 4/2002 | Jackson |
| 6,379,356 B1 | 4/2002 | Jackson |
| 6,402,757 B1 | 6/2002 | Moore et al. |
| 6,440,133 B1 | 8/2002 | Beale et al. |
| 6,443,956 B1 | 9/2002 | Ray |
| 6,467,958 B1 | 10/2002 | Sasaki et al. |
| 6,471,703 B1 | 10/2002 | Ashman |
| 6,478,797 B1 | 11/2002 | Paul |

(56) References Cited

U.S. PATENT DOCUMENTS

| | | |
|---|---|---|
| 6,478,798 B1 | 11/2002 | Howland |
| 6,485,491 B1 | 11/2002 | Farris et al. |
| 6,485,492 B1 | 11/2002 | Halm et al. |
| 6,485,494 B1 | 11/2002 | Haider |
| 6,520,962 B1 | 2/2003 | Taylor et al. |
| 6,527,804 B1 | 3/2003 | Gauchet et al. |
| 6,533,786 B1 | 3/2003 | Needham et al. |
| 6,554,831 B1 | 4/2003 | Rivard et al. |
| 6,554,834 B1 | 4/2003 | Crozet et al. |
| 6,562,040 B1 | 5/2003 | Wagner |
| 6,565,565 B1 | 5/2003 | Yuan et al. |
| 6,565,567 B1 | 5/2003 | Haider |
| 6,595,992 B1 | 7/2003 | Wagner et al. |
| 6,602,255 B1 | 8/2003 | Campbell et al. |
| 6,613,050 B1 | 9/2003 | Wagner et al. |
| 6,616,667 B1 | 9/2003 | Steiger et al. |
| 6,648,885 B1 | 11/2003 | Friesem |
| 6,648,888 B1 | 11/2003 | Shluzas |
| 6,652,526 B1 | 11/2003 | Arafiles |
| 6,652,765 B1 | 11/2003 | Beaty |
| 6,656,179 B1 | 12/2003 | Schaefer et al. |
| 6,663,632 B1 | 12/2003 | Frigg |
| 6,673,073 B1 | 1/2004 | Schaefer |
| 6,676,661 B1 | 1/2004 | Benlloch et al. |
| 6,712,818 B1 | 3/2004 | Michelson |
| 6,716,214 B1 | 4/2004 | Jackson |
| 6,743,231 B1 | 6/2004 | Gray et al. |
| 6,755,829 B1 | 6/2004 | Bono et al. |
| 6,778,861 B1 | 8/2004 | Liebrecht et al. |
| 6,872,208 B1 | 3/2005 | McBride et al. |
| 6,896,677 B1 | 5/2005 | Lin |
| 7,001,389 B1 | 2/2006 | Navarro et al. |
| RE39,035 E | 3/2006 | Finn et al. |
| RE39,089 E | 5/2006 | Ralph et al. |
| 7,081,116 B1 | 7/2006 | Carly |
| 7,316,684 B1 | 1/2008 | Baccelli et al. |
| 7,377,923 B2 * | 5/2008 | Purcell et al. ............. 606/248 |
| 7,686,833 B1 | 3/2010 | Muhanna et al. |
| 7,766,943 B1 | 8/2010 | Fallin et al. |
| 7,833,251 B1 | 11/2010 | Ahlgren et al. |
| 8,043,340 B1 | 10/2011 | Law |
| 8,092,499 B1 | 1/2012 | Roth |
| 8,167,914 B1 | 5/2012 | Hunt et al. |
| 8,197,517 B1 | 6/2012 | Lab et al. |
| 8,211,110 B1 | 7/2012 | Corin et al. |
| 8,236,035 B1 | 8/2012 | Bedor |
| 8,298,265 B2 * | 10/2012 | Purcell et al. ............. 606/246 |
| 8,388,659 B1 | 3/2013 | Lab et al. |
| 8,439,924 B1 | 5/2013 | McBride et al. |
| 8,470,009 B1 | 6/2013 | Rezach |
| 8,636,775 B2 * | 1/2014 | Purcell et al. ............. 606/264 |
| 2001/0007941 A1 | 7/2001 | Steiner et al. |
| 2001/0010000 A1 | 7/2001 | Gertzbein et al. |
| 2001/0011172 A1 | 8/2001 | Orbay et al. |
| 2001/0012937 A1 | 8/2001 | Schaffler-Wachter et al. |
| 2001/0023350 A1 | 9/2001 | Choi |
| 2001/0037111 A1 | 11/2001 | Dixon et al. |
| 2001/0041894 A1 | 11/2001 | Campbell et al. |
| 2001/0047173 A1 | 11/2001 | Schlapfer et al. |
| 2001/0047174 A1 | 11/2001 | Donno et al. |
| 2001/0047175 A1 | 11/2001 | Doubler et al. |
| 2001/0052438 A1 | 12/2001 | Spencer |
| 2002/0004683 A1 | 1/2002 | Michelson |
| 2002/0007184 A1 | 1/2002 | Ogilvie et al. |
| 2002/0010467 A1 | 1/2002 | Cooper et al. |
| 2002/0013586 A1 | 1/2002 | Justis et al. |
| 2002/0016594 A1 | 2/2002 | Schlapfer et al. |
| 2002/0022764 A1 | 2/2002 | Smith et al. |
| 2002/0022842 A1 | 2/2002 | Horvath et al. |
| 2002/0029040 A1 | 3/2002 | Morrison et al. |
| 2002/0035365 A1 | 3/2002 | Kumar et al. |
| 2002/0035366 A1 | 3/2002 | Walder et al. |
| 2002/0035367 A1 | 3/2002 | Ritland |
| 2002/0045898 A1 | 4/2002 | Freid et al. |
| 2002/0045899 A1 | 4/2002 | Errico et al. |
| 2002/0049446 A1 | 4/2002 | Harkey, III et al. |
| 2002/0055740 A1 | 5/2002 | Lieberman |
| 2002/0055741 A1 | 5/2002 | Schlapfer et al. |
| 2002/0058942 A1 | 5/2002 | Biedermann et al. |
| 2002/0068975 A1 | 6/2002 | Teitelbaum et al. |
| 2002/0072750 A1 | 6/2002 | Jackson |
| 2002/0072751 A1 | 6/2002 | Jackson |
| 2002/0082602 A1 | 6/2002 | Biedermann et al. |
| 2002/0082603 A1 | 6/2002 | Dixon et al. |
| 2002/0087159 A1 | 7/2002 | Thomas |
| 2002/0087161 A1 | 7/2002 | Randall et al. |
| 2002/0091386 A1 | 7/2002 | Martin et al. |
| 2002/0095153 A1 | 7/2002 | Jones et al. |
| 2002/0095154 A1 | 7/2002 | Atkinson et al. |
| 2002/0095881 A1 | 7/2002 | Shreiner |
| 2002/0103487 A1 | 8/2002 | Errico et al. |
| 2002/0111627 A1 | 8/2002 | Vincent-Prestigiancomo |
| 2002/0116001 A1 | 8/2002 | Schaefer et al. |
| 2002/0120270 A1 | 8/2002 | Trieu et al. |
| 2002/0123752 A1 | 9/2002 | Schultheiss et al. |
| 2002/0133154 A1 | 9/2002 | Saint Martin |
| 2002/0133158 A1 | 9/2002 | Saint Martin |
| 2002/0133159 A1 | 9/2002 | Jackson |
| 2002/0138076 A1 | 9/2002 | Biedermann et al. |
| 2002/0138077 A1 | 9/2002 | Ferree |
| 2002/0143328 A1 | 10/2002 | Shluzas et al. |
| 2002/0143330 A1 | 10/2002 | Shluzas |
| 2002/0143332 A1 | 10/2002 | Lin et al. |
| 2002/0143338 A1 | 10/2002 | Orbay et al. |
| 2002/0143341 A1 | 10/2002 | Biedermann et al. |
| 2002/0161368 A1 | 10/2002 | Foley et al. |
| 2002/0161370 A1 | 10/2002 | Frigg et al. |
| 2002/0173791 A1 | 11/2002 | Howland |
| 2002/0183747 A1 | 12/2002 | Jao et al. |
| 2002/0198526 A1 | 12/2002 | Shaolian et al. |
| 2003/0004519 A1 | 1/2003 | Torode et al. |
| 2003/0023243 A1 | 1/2003 | Biedermann et al. |
| 2003/0028191 A1 | 2/2003 | Shluzas |
| 2003/0032957 A1 | 2/2003 | McKinley |
| 2003/0055426 A1 | 3/2003 | Carbone et al. |
| 2003/0055427 A1 | 3/2003 | Graf |
| 2003/0060826 A1 | 3/2003 | Foley et al. |
| 2003/0073995 A1 | 4/2003 | Reed |
| 2003/0073996 A1 | 4/2003 | Doubler et al. |
| 2003/0073998 A1 | 4/2003 | Pagliuca et al. |
| 2003/0078580 A1 | 4/2003 | Shitoto |
| 2003/0083657 A1 | 5/2003 | Drewry et al. |
| 2003/0083667 A1 | 5/2003 | Ralph et al. |
| 2003/0093077 A1 | 5/2003 | Schlapfer et al. |
| 2003/0093078 A1 | 5/2003 | Ritland |
| 2003/0100896 A1 | 5/2003 | Biedermann et al. |
| 2003/0100897 A1 | 5/2003 | Metz-Stavenhagen |
| 2003/0100904 A1 | 5/2003 | Biedermann |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0120275 A1 | 6/2003 | Lenke et al. |
| 2003/0125741 A1 | 7/2003 | Biedermann et al. |
| 2003/0125749 A1 | 7/2003 | Yuan et al. |
| 2003/0130659 A1 | 7/2003 | Haider |
| 2003/0130661 A1 | 7/2003 | Osman |
| 2003/0135210 A1 | 7/2003 | Dixon et al. |
| 2003/0135217 A1 | 7/2003 | Buttermann et al. |
| 2003/0139745 A1 | 7/2003 | Ashman |
| 2003/0149431 A1 | 8/2003 | Varieur |
| 2003/0149432 A1 | 8/2003 | Frigg et al. |
| 2003/0149435 A1 | 8/2003 | Baynham et al. |
| 2003/0153911 A1 | 8/2003 | Shluzas |
| 2003/0153912 A1 | 8/2003 | Graf |
| 2003/0153920 A1 | 8/2003 | Ralph et al. |
| 2003/0163133 A1 | 8/2003 | Altarac et al. |
| 2003/0167058 A1 | 9/2003 | Shluzas |
| 2003/0171749 A1 | 9/2003 | Le Couedic et al. |
| 2003/0176863 A1 | 9/2003 | Ueyama et al. |
| 2003/0181913 A1 | 9/2003 | Lieberman |
| 2003/0187433 A1 | 10/2003 | Lin |
| 2003/0187434 A1 | 10/2003 | Lin |
| 2003/0191470 A1 | 10/2003 | Ritland |
| 2003/0199872 A1 | 10/2003 | Markworth et al. |

(56) References Cited

U.S. PATENT DOCUMENTS

| | | |
|---|---|---|
| 2003/0199873 A1 | 10/2003 | Richelsoph |
| 2003/0208204 A1 | 11/2003 | Bailey et al. |
| 2003/0212398 A1 | 11/2003 | Jackson |
| 2003/0216735 A1 | 11/2003 | Altarac et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2003/0229345 A1 | 12/2003 | Stahurski |
| 2003/0229347 A1 | 12/2003 | Sherman et al. |
| 2003/0236529 A1 | 12/2003 | Shluzas et al. |
| 2004/0006342 A1 | 1/2004 | Altarac et al. |
| 2004/0039384 A1 | 2/2004 | Boehm, Jr. et al. |
| 2004/0039385 A1 | 2/2004 | Mazda et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0073218 A1 | 4/2004 | Dahners |
| 2004/0078051 A1 | 4/2004 | Davison et al. |
| 2004/0078082 A1 | 4/2004 | Lange |
| 2004/0220671 A1 | 4/2004 | Ralph et al. |
| 2004/0087949 A1 | 5/2004 | Bono et al. |
| 2004/0087950 A1 | 5/2004 | Teitelbaum |
| 2004/0087952 A1 | 5/2004 | Borgstrom et al. |
| 2004/0092934 A1 | 5/2004 | Howland |
| 2004/0092938 A1 | 5/2004 | Carli |
| 2004/0097933 A1 | 5/2004 | Lourdel et al. |
| 2004/0106925 A1 | 6/2004 | Culbert |
| 2004/0111091 A1 | 6/2004 | Ogilvie et al. |
| 2004/0122442 A1 | 6/2004 | Lewis |
| 2004/0127904 A1 | 7/2004 | Konieczynski et al. |
| 2004/0133207 A1 | 7/2004 | Abdou |
| 2004/0138660 A1 | 7/2004 | Serhan |
| 2004/0138662 A1 | 7/2004 | Landry et al. |
| 2004/0147928 A1 | 7/2004 | Landry et al. |
| 2004/0147929 A1 | 7/2004 | Biedermann et al. |
| 2004/0147937 A1 | 7/2004 | Dunbar, Jr. et al. |
| 2004/0153068 A1 | 8/2004 | Janowski et al. |
| 2004/0158245 A1 | 8/2004 | Chin |
| 2004/0158247 A1 | 8/2004 | Sitiso et al. |
| 2004/0158258 A1 | 8/2004 | Bonati et al. |
| 2004/0162560 A1 | 8/2004 | Raynor et al. |
| 2004/0167523 A1 | 8/2004 | Jackson |
| 2004/0167525 A1 | 8/2004 | Jackson |
| 2004/0172025 A1 | 9/2004 | Drewry et al. |
| 2004/0172031 A1 | 9/2004 | Rubecamp et al. |
| 2004/0172032 A1 | 9/2004 | Jackson |
| 2004/0176776 A1 | 9/2004 | Zubok et al. |
| 2004/0186473 A1 | 9/2004 | Cournoyer et al. |
| 2004/0186474 A1 | 9/2004 | Matthis et al. |
| 2004/0186475 A1 | 9/2004 | Falahee |
| 2004/0210216 A1 | 10/2004 | Farris et al. |
| 2004/0210227 A1 | 10/2004 | Trail et al. |
| 2004/0215190 A1 | 10/2004 | Nguyen et al. |
| 2004/0215191 A1 | 10/2004 | Kitchen |
| 2004/0220567 A1 | 11/2004 | Eisermann et al. |
| 2004/0225289 A1 | 11/2004 | Biedermann et al. |
| 2004/0230100 A1 | 11/2004 | Shluzas |
| 2004/0236327 A1 | 11/2004 | Paul et al. |
| 2004/0236328 A1 | 11/2004 | Paul et al. |
| 2004/0236330 A1 | 11/2004 | Purcell et al. |
| 2004/0249378 A1 | 12/2004 | Saint Martin et al. |
| 2004/0254574 A1 | 12/2004 | Morrison et al. |
| 2004/0260283 A1 | 12/2004 | Wu et al. |
| 2004/0267264 A1 | 12/2004 | Konieczynski et al. |
| 2005/0010219 A1 | 1/2005 | Dalton |
| 2005/0027296 A1 | 2/2005 | Thramann et al. |
| 2005/0033298 A1 | 2/2005 | Hawkes et al. |
| 2005/0033436 A1 | 2/2005 | Schlapfer et al. |
| 2005/0033439 A1 | 2/2005 | Gordon et al. |
| 2005/0038430 A1 | 2/2005 | McKinley |
| 2005/0038432 A1 | 2/2005 | Shaolian et al. |
| 2005/0038433 A1 | 2/2005 | Young |
| 2005/0049588 A1 | 3/2005 | Jackson |
| 2005/0049589 A1 | 3/2005 | Jackson |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0070901 A1 | 3/2005 | David |
| 2005/0080415 A1 | 4/2005 | Keyer et al. |
| 2005/0085812 A1 | 4/2005 | Sherman et al. |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0090821 A1 | 4/2005 | Berrevoets et al. |
| 2005/0096652 A1 | 5/2005 | Burton |
| 2005/0096653 A1 | 5/2005 | Doubler et al. |
| 2005/0096654 A1 | 5/2005 | Lin |
| 2005/0107788 A1 | 5/2005 | Beaurain et al. |
| 2005/0113927 A1 | 5/2005 | Malek |
| 2005/0119658 A1 | 6/2005 | Ralph et al. |
| 2005/0124991 A1 | 6/2005 | Jahng |
| 2005/0131404 A1 | 6/2005 | Mazda et al. |
| 2005/0131405 A1 | 6/2005 | Molz, IV et al. |
| 2005/0131406 A1 | 6/2005 | Reiley et al. |
| 2005/0131407 A1 | 6/2005 | Sicvol et al. |
| 2005/0131408 A1 | 6/2005 | Sicvol et al. |
| 2005/0131413 A1 | 6/2005 | O'Driscoll et al. |
| 2005/0131419 A1 | 6/2005 | McCord et al. |
| 2005/0131422 A1 | 6/2005 | Anderson |
| 2005/0137594 A1 | 6/2005 | Doubler et al. |
| 2005/0137597 A1 | 6/2005 | Butler et al. |
| 2005/0141986 A1 | 6/2005 | Flesher |
| 2005/0143737 A1 | 6/2005 | Pafford et al. |
| 2005/0143823 A1 | 6/2005 | Boyd et al. |
| 2005/0144389 A1 | 7/2005 | Selover et al. |
| 2005/0149020 A1 | 7/2005 | Jahng |
| 2005/0149053 A1 | 7/2005 | Varieur |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177154 A1 | 8/2005 | Moumene et al. |
| 2005/0177166 A1 | 8/2005 | Timm et al. |
| 2005/0182401 A1 | 8/2005 | Timm et al. |
| 2005/0182410 A1 | 8/2005 | Jackson |
| 2005/0187548 A1 | 8/2005 | Butler et al. |
| 2005/0187555 A1 | 8/2005 | Biedermann et al. |
| 2005/0192571 A1 | 9/2005 | Abdelgany |
| 2005/0192572 A1 | 9/2005 | Abdelgany et al. |
| 2005/0192573 A1 | 9/2005 | Abdelgany et al. |
| 2005/0192579 A1 | 9/2005 | Jackson |
| 2005/0192580 A1 | 9/2005 | Dalton |
| 2005/0192589 A1 | 9/2005 | Raymond et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Harms et al. |
| 2005/0203518 A1 | 9/2005 | Biederman et al. |
| 2005/0203519 A1 | 9/2005 | Harms et al. |
| 2005/0215999 A1 | 9/2005 | Birkmeyer et al. |
| 2005/0216000 A1 | 9/2005 | Colleran et al. |
| 2005/0216001 A1 | 9/2005 | David |
| 2005/0216003 A1 | 9/2005 | Biedermann et al. |
| 2005/0228326 A1 | 10/2005 | Kalfas et al. |
| 2005/0228379 A1 | 10/2005 | Jackson |
| 2005/0228385 A1 | 10/2005 | Lee et al. |
| 2005/0228400 A1 | 10/2005 | Chao |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0234459 A1 | 10/2005 | Falahee et al. |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |

(56) References Cited

U.S. PATENT DOCUMENTS

| | | |
|---|---|---|
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0260058 A1 | 11/2005 | Casagne, III |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267472 A1 | 12/2005 | Biedermann et al. |
| 2005/0267474 A1 | 12/2005 | Dalton |
| 2005/0267477 A1 | 12/2005 | Jackson |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0278023 A1 | 12/2005 | Zwirkoski |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi |
| 2005/0288672 A1 | 12/2005 | Ferree |
| 2005/0288673 A1 | 12/2005 | Catbagan et al. |
| 2006/0004359 A1 | 1/2006 | Kramer et al. |
| 2006/0004363 A1 | 1/2006 | Brockmeyer et al. |
| 2006/0009767 A1 | 1/2006 | Kiester |
| 2006/0009769 A1 | 1/2006 | Lieberman |
| 2006/0009770 A1 | 1/2006 | Speirs et al. |
| 2006/0009780 A1 | 1/2006 | Foley et al. |
| 2006/0015099 A1 | 1/2006 | Cannon et al. |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0025771 A1 | 2/2006 | Jackson |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036243 A1 | 2/2006 | Sasso et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg et al. |
| 2006/0074418 A1 | 4/2006 | Jackson |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak et al. |
| 2006/0079898 A1 | 4/2006 | Ainsworth |
| 2006/0079899 A1 | 4/2006 | Ritland |
| 2006/0084977 A1 | 4/2006 | Liberman |
| 2006/0084980 A1 | 4/2006 | Melkent et al. |
| 2006/0084981 A1 | 4/2006 | Shluzas |
| 2006/0084982 A1 | 4/2006 | Dickinson et al. |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0089643 A1 | 4/2006 | Mujwid |
| 2006/0089644 A1 | 4/2006 | Felix |
| 2006/0089645 A1 | 4/2006 | Eckman |
| 2006/0095035 A1 | 5/2006 | Jones et al. |
| 2006/0095037 A1 | 5/2006 | Jones et al. |
| 2006/0095038 A1 | 5/2006 | Jackson |
| 2006/0100621 A1 | 5/2006 | Jackson |
| 2006/0100622 A1 | 5/2006 | Jackson |
| 2006/0106381 A1 | 5/2006 | Ferree et al. |
| 2006/0106394 A1 | 5/2006 | Colleran |
| 2006/0111713 A1 | 5/2006 | Jackson |
| 2006/0111715 A1 | 5/2006 | Jackson |
| 2006/0116677 A1 | 6/2006 | Burd et al. |
| 2006/0122597 A1 | 6/2006 | Jones et al. |
| 2006/0122599 A1 | 6/2006 | Drewry et al. |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0131421 A1 | 6/2006 | Dunn et al. |
| 2006/0142758 A1 | 6/2006 | Petit |
| 2006/0142760 A1 | 6/2006 | McDonnell |
| 2006/0149228 A1 | 7/2006 | Schlapfer et al. |
| 2006/0149229 A1 | 7/2006 | Kwak et al. |
| 2006/0149238 A1 | 7/2006 | Sherman et al. |
| 2006/0149240 A1 | 7/2006 | Jackson |
| 2006/0149241 A1 | 7/2006 | Richelsoph et al. |
| 2006/0149251 A1 | 7/2006 | Ziolo et al. |
| 2006/0155277 A1 | 7/2006 | Metz-Stavenhagen |
| 2006/0161152 A1 | 7/2006 | Ensign et al. |
| 2006/0166535 A1 | 7/2006 | Brumfield et al. |
| 2006/0167454 A1 | 7/2006 | Ludwig et al. |
| 2006/0167455 A1 | 7/2006 | Clement et al. |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189983 A1 | 8/2006 | Fallin et al. |
| 2006/0189985 A1 | 8/2006 | Lewis |
| 2006/0195090 A1 | 8/2006 | Suddaby |
| 2006/0195093 A1 | 8/2006 | Jahng |
| 2006/0195198 A1 | 8/2006 | James |
| 2006/0200023 A1 | 9/2006 | Melkent et al. |
| 2006/0200130 A1 | 9/2006 | Hawkins et al. |
| 2006/0200131 A1 | 9/2006 | Chao et al. |
| 2006/0200132 A1 | 9/2006 | Chao et al. |
| 2006/0200133 A1 | 9/2006 | Jackson |
| 2006/0200149 A1 | 9/2006 | Hoy et al. |
| 2006/0212033 A1 | 9/2006 | Rothman et al. |
| 2006/0212034 A1 | 9/2006 | Triplett et al. |
| 2006/0217713 A1 | 9/2006 | Serhan et al. |
| 2006/0217716 A1 | 9/2006 | Baker et al. |
| 2006/0217719 A1 | 9/2006 | Albert et al. |
| 2006/0229608 A1 | 10/2006 | Foster et al. |
| 2006/0229609 A1 | 10/2006 | Wang |
| 2006/0229613 A1 | 10/2006 | Timm |
| 2006/0229614 A1 | 10/2006 | Foley et al. |
| 2006/0229615 A1 | 10/2006 | Abdou |
| 2006/0241593 A1 | 10/2006 | Sherman et al. |
| 2006/0241595 A1 | 10/2006 | Molz, IV et al. |
| 2006/0241600 A1 | 10/2006 | Ensign et al. |
| 2006/0241601 A1 | 10/2006 | Trautwein et al. |
| 2006/0241603 A1 | 10/2006 | Jackson |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow et al. |
| 2006/0247633 A1 | 11/2006 | Winslow et al. |
| 2006/0247658 A1 | 11/2006 | Pond, Jr. et al. |
| 2006/0260483 A1 | 11/2006 | Hartmann et al. |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264962 A1 | 11/2006 | Chin et al. |

(56) References Cited

U.S. PATENT DOCUMENTS

| | | |
|---|---|---|
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282075 A1 | 12/2006 | Labrom et al. |
| 2006/0282076 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293666 A1 | 12/2006 | Matthis et al. |
| 2006/0293693 A1 | 12/2006 | Farr et al. |
| 2007/0005062 A1 | 1/2007 | Lange et al. |
| 2007/0005063 A1 | 1/2007 | Bruneau et al. |
| 2007/0005137 A1 | 1/2007 | Kwak |
| 2007/0016190 A1 | 1/2007 | Martinez et al. |
| 2007/0016194 A1 | 1/2007 | Shaolian et al. |
| 2007/0016200 A1 | 1/2007 | Jackson |
| 2007/0021750 A1 | 1/2007 | Shluzas et al. |
| 2007/0032123 A1 | 2/2007 | Timm et al. |
| 2007/0043356 A1 | 2/2007 | Timm et al. |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049931 A1 | 3/2007 | Justis et al. |
| 2007/0049933 A1 | 3/2007 | Ahn et al. |
| 2007/0049936 A1 | 3/2007 | Colleran et al. |
| 2007/0055236 A1 | 3/2007 | Hudgins et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0073289 A1 | 3/2007 | Kwak et al. |
| 2007/0073290 A1 | 3/2007 | Boehm, Jr. |
| 2007/0073291 A1 | 3/2007 | Cordaro et al. |
| 2007/0073293 A1 | 3/2007 | Math et al. |
| 2007/0073294 A1 | 3/2007 | Chin et al. |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0090238 A1 | 4/2007 | Justis |
| 2007/0093813 A1 | 4/2007 | Callahan et al. |
| 2007/0093814 A1 | 4/2007 | Callahan, II et al. |
| 2007/0093815 A1 | 4/2007 | Callahan, II et al. |
| 2007/0093818 A1 | 4/2007 | Biedermann et al. |
| 2007/0093819 A1 | 4/2007 | Albert |
| 2007/0093824 A1 | 4/2007 | Hestad et al. |
| 2007/0093826 A1 | 4/2007 | Hawkes et al. |
| 2007/0093833 A1 | 4/2007 | Kuiper et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123867 A1 | 5/2007 | Kirschman |
| 2007/0123870 A1 | 5/2007 | Jeon et al. |
| 2007/0156142 A1 | 7/2007 | Rezach et al. |
| 2007/0161986 A1 | 7/2007 | Levy |
| 2007/0161991 A1 | 7/2007 | Altarac et al. |
| 2007/0161994 A1 | 7/2007 | Lowrey et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191832 A1 | 8/2007 | Trieu |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0225707 A1 | 9/2007 | Wisnewski et al. |
| 2007/0225708 A1 | 9/2007 | Biedermann et al. |
| 2007/0225711 A1 | 9/2007 | Ensign |
| 2007/0233073 A1 | 10/2007 | Wisnewski et al. |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233089 A1 | 10/2007 | Dipoto et al. |
| 2007/0233092 A1 | 10/2007 | Falahee |
| 2007/0233094 A1 | 10/2007 | Colleran et al. |
| 2007/0233095 A1 | 10/2007 | Schlapfer |
| 2007/0233155 A1 | 10/2007 | Lovell |
| 2007/0244481 A1 | 10/2007 | Timm |
| 2007/0244482 A1 | 10/2007 | Aferzon |
| 2007/0250061 A1 | 10/2007 | Chin et al. |
| 2007/0260243 A1 | 11/2007 | Kagami |
| 2007/0270813 A1 | 11/2007 | Garamszegi |
| 2007/0270821 A1 | 11/2007 | Trieu et al. |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0270843 A1 | 11/2007 | Matthis et al. |
| 2007/0270869 A1 | 11/2007 | Young et al. |
| 2007/0276371 A1 | 11/2007 | Baynham et al. |
| 2007/0276379 A1 | 11/2007 | Miller et al. |
| 2007/0276380 A1 | 11/2007 | Jahng et al. |
| 2007/0288004 A1 | 12/2007 | Alvarez |
| 2007/0288012 A1 | 12/2007 | Colleran et al. |
| 2007/0293862 A1 | 12/2007 | Jackson |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015597 A1 | 1/2008 | Whipple |
| 2008/0021454 A1 | 1/2008 | Chao et al. |
| 2008/0021455 A1 | 1/2008 | Chao et al. |
| 2008/0021462 A1 | 1/2008 | Trieu |
| 2008/0021464 A1 | 1/2008 | Morin et al. |
| 2008/0021465 A1 | 1/2008 | Shadduck et al. |
| 2008/0027432 A1 | 1/2008 | Strauss et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0077136 A1 | 3/2008 | Triplett et al. |
| 2008/0077138 A1 | 3/2008 | Cohen et al. |
| 2008/0077139 A1 | 3/2008 | Landry et al. |
| 2008/0077143 A1 | 3/2008 | Shluzas |
| 2008/0086131 A1 | 4/2008 | Daly et al. |
| 2008/0086132 A1 | 4/2008 | Biedermann et al. |
| 2008/0091213 A1 | 4/2008 | Jackson |
| 2008/0097441 A1 | 4/2008 | Hayes et al. |
| 2008/0103502 A1 | 5/2008 | Capote et al. |
| 2008/0108992 A1 | 5/2008 | Barry et al. |

(56) References Cited

U.S. PATENT DOCUMENTS

| | | |
|---|---|---|
| 2008/0114362 A1 | 5/2008 | Justis et al. |
| 2008/0114403 A1 | 5/2008 | Kuester et al. |
| 2008/0119849 A1 | 5/2008 | Beardsley et al. |
| 2008/0119857 A1 | 5/2008 | Potash et al. |
| 2008/0125777 A1 | 5/2008 | Veldman et al. |
| 2008/0125787 A1 | 5/2008 | Doubler et al. |
| 2008/0125813 A1 | 5/2008 | Erickson et al. |
| 2008/0132957 A1 | 6/2008 | Matthis et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0140136 A1 | 6/2008 | Jackson |
| 2008/0147121 A1 | 6/2008 | Justis et al. |
| 2008/0147122 A1 | 6/2008 | Jackson |
| 2008/0147129 A1 | 6/2008 | Biedermann et al. |
| 2008/0147195 A1 | 6/2008 | Kwak et al. |
| 2008/0154279 A1 | 6/2008 | Schumaker et al. |
| 2008/0154308 A1 | 6/2008 | Sherman et al. |
| 2008/0154315 A1 | 6/2008 | Jackson |
| 2008/0161857 A1 | 7/2008 | Hestad et al. |
| 2008/0161863 A1 | 7/2008 | Arnold et al. |
| 2008/0167687 A1 | 7/2008 | Colleran et al. |
| 2008/0172090 A1 | 7/2008 | Molz |
| 2008/0172091 A1 | 7/2008 | Anderson |
| 2008/0172096 A1 | 7/2008 | Hawkins |
| 2008/0177316 A1 | 7/2008 | Bergeron et al. |
| 2008/0177317 A1 | 7/2008 | Jackson |
| 2008/0177321 A1 | 7/2008 | Drewry et al. |
| 2008/0177322 A1 | 7/2008 | Davis et al. |
| 2008/0177323 A1 | 7/2008 | Null et al. |
| 2008/0177388 A1 | 7/2008 | Patterson et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183219 A1 | 7/2008 | Jackson |
| 2008/0183223 A1 | 7/2008 | Jeon et al. |
| 2008/0188898 A1 | 8/2008 | Jackson |
| 2008/0195153 A1 | 8/2008 | Thompson |
| 2008/0195155 A1 | 8/2008 | Hoffman et al. |
| 2008/0195159 A1 | 8/2008 | Kloss et al. |
| 2008/0200918 A1 | 8/2008 | Spitler et al. |
| 2008/0200956 A1 | 8/2008 | Beckwith et al. |
| 2008/0215095 A1 | 9/2008 | Biedermann et al. |
| 2008/0215100 A1 | 9/2008 | Matthis et al. |
| 2008/0228184 A1 | 9/2008 | Hestad |
| 2008/0228228 A1 | 9/2008 | Hestad et al. |
| 2008/0234736 A1 | 9/2008 | Trieu et al. |
| 2008/0234737 A1 | 9/2008 | Boschert |
| 2008/0234738 A1 | 9/2008 | Zylber et al. |
| 2008/0234739 A1 | 9/2008 | Hudgins et al. |
| 2008/0234744 A1 | 9/2008 | Zylber et al. |
| 2008/0234756 A1 | 9/2008 | Sutcliffe et al. |
| 2008/0234759 A1 | 9/2008 | Marino |
| 2008/0234761 A1 | 9/2008 | Jackson |
| 2008/0243052 A1 | 10/2008 | Pond et al. |
| 2008/0243185 A1 | 10/2008 | Felix et al. |
| 2008/0243193 A1 | 10/2008 | Ensign et al. |
| 2008/0249570 A1 | 10/2008 | Carson et al. |
| 2008/0262548 A1 | 10/2008 | Lange et al. |
| 2008/0262551 A1 | 10/2008 | Rice et al. |
| 2008/0262554 A1 | 10/2008 | Hayes et al. |
| 2008/0262556 A1 | 10/2008 | Jacofsky et al. |
| 2008/0269742 A1 | 10/2008 | Levy et al. |
| 2008/0269804 A1 | 10/2008 | Holt |
| 2008/0269805 A1 | 10/2008 | Dekutoski et al. |
| 2008/0275456 A1 | 11/2008 | Vonwiller et al. |
| 2008/0275504 A1 | 11/2008 | Bonin et al. |
| 2008/0287994 A1 | 11/2008 | Perez-Cruet et al. |
| 2008/0288002 A1 | 11/2008 | Crall et al. |
| 2008/0294203 A1 | 11/2008 | Kovach et al. |
| 2008/0300630 A1 | 12/2008 | Bonnema et al. |
| 2008/0300631 A1 | 12/2008 | Tornier |
| 2008/0300633 A1 | 12/2008 | Jackson |
| 2008/0306513 A1 | 12/2008 | Winslow et al. |
| 2008/0306525 A1 | 12/2008 | Winslow et al. |
| 2008/0306526 A1 | 12/2008 | Winslow et al. |
| 2008/0306533 A1 | 12/2008 | Winslow et al. |
| 2008/0306536 A1 | 12/2008 | Frigg et al. |
| 2008/0306540 A1 | 12/2008 | Mitchell et al. |
| 2008/0306543 A1 | 12/2008 | Cain et al. |
| 2008/0312655 A1 | 12/2008 | Kirschman et al. |
| 2008/0312692 A1 | 12/2008 | Brennan et al. |
| 2008/0312696 A1 | 12/2008 | Butters et al. |
| 2008/0312701 A1 | 12/2008 | Butters et al. |
| 2008/0312703 A1 | 12/2008 | Hestad et al. |
| 2008/0312704 A1 | 12/2008 | Hestad et al. |
| 2008/0319482 A1 | 12/2008 | Jackson |
| 2008/0319490 A1 | 12/2008 | Jackson |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0012567 A1 | 1/2009 | Biedermann et al. |
| 2009/0018557 A1 | 1/2009 | Pisharodi |
| 2009/0018583 A1 | 1/2009 | Song et al. |
| 2009/0024165 A1 | 1/2009 | Ferree |
| 2009/0024169 A1 | 1/2009 | Triplett et al. |
| 2009/0030457 A1 | 1/2009 | Janowski et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0048601 A1 | 2/2009 | Forton et al. |
| 2009/0048631 A1 | 2/2009 | Bhatnagar et al. |
| 2009/0062860 A1 | 3/2009 | Fraiser et al. |
| 2009/0062865 A1 | 3/2009 | Schumacher |
| 2009/0062866 A1 | 3/2009 | Jackson |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082666 A1 | 3/2009 | Geist et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088769 A1 | 4/2009 | Poletti |
| 2009/0088799 A1 | 4/2009 | Yeh |
| 2009/0088803 A1 | 4/2009 | Justis et al. |
| 2009/0088807 A1 | 4/2009 | Castaneda et al. |
| 2009/0093820 A1 | 4/2009 | Trieu et al. |
| 2009/0093843 A1 | 4/2009 | Lemoine et al. |
| 2009/0093846 A1 | 4/2009 | Hestad et al. |
| 2009/0099606 A1 | 4/2009 | Hestad et al. |
| 2009/0099608 A1 | 4/2009 | Szczesny |
| 2009/0105769 A1 | 4/2009 | Rock et al. |
| 2009/0105770 A1 | 4/2009 | Berrevoets et al. |
| 2009/0105771 A1 | 4/2009 | Lei et al. |
| 2009/0105820 A1 | 4/2009 | Jackson |
| 2009/0112265 A1 | 4/2009 | Hudgins et al. |
| 2009/0112266 A1 | 4/2009 | Weng et al. |
| 2009/0112269 A1 | 4/2009 | Lieberman et al. |
| 2009/0118772 A1 | 5/2009 | Diederich et al. |
| 2009/0131983 A1 | 5/2009 | Biedermann et al. |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143828 A1 | 6/2009 | Stad et al. |
| 2009/0149885 A1 | 6/2009 | Durward et al. |
| 2009/0149892 A1 | 6/2009 | Stad et al. |
| 2009/0157120 A1 | 6/2009 | Marino et al. |
| 2009/0163901 A1 | 6/2009 | Fisher et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0171392 A1 | 7/2009 | Garcia-Bengochea et al. |
| 2009/0171395 A1 | 7/2009 | Jeon et al. |
| 2009/0177232 A1 | 7/2009 | Kiester |
| 2009/0177237 A1 | 7/2009 | Zucherman et al. |
| 2009/0182380 A1 | 7/2009 | Abdelgany |

(56) References Cited

U.S. PATENT DOCUMENTS

| | | |
|---|---|---|
| 2009/0182430 A1 | 7/2009 | Tyber et al. |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198281 A1 | 8/2009 | Rice et al. |
| 2009/0198289 A1 | 8/2009 | Manderson |
| 2009/0198291 A1 | 8/2009 | Kevin et al. |
| 2009/0216278 A1 | 8/2009 | Song |
| 2009/0216280 A1 | 8/2009 | Hutchinson |
| 2009/0221877 A1 | 9/2009 | Woods |
| 2009/0228045 A1 | 9/2009 | Hayes et al. |
| 2009/0240292 A1 | 9/2009 | Butler et al. |
| 2009/0248030 A1 | 10/2009 | Butler et al. |
| 2009/0248075 A1 | 10/2009 | Ogilvie et al. |
| 2009/0248077 A1 | 10/2009 | Johns |
| 2009/0248083 A1 | 10/2009 | Patterson et al. |
| 2009/0248088 A1 | 10/2009 | Biedermann |
| 2009/0254125 A1 | 10/2009 | Predick |
| 2009/0259254 A1 | 10/2009 | Pisharodi |
| 2009/0259257 A1 | 10/2009 | Prevost |
| 2009/0259258 A1 | 10/2009 | Perez-Cruet et al. |
| 2009/0264895 A1 | 10/2009 | Gasperut et al. |
| 2009/0264896 A1 | 10/2009 | Biedermann et al. |
| 2009/0264930 A1 | 10/2009 | McBride |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275985 A1 | 11/2009 | Jackson |
| 2009/0275986 A1 | 11/2009 | Prevost et al. |
| 2009/0281542 A1 | 11/2009 | Justis |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0281574 A1 | 11/2009 | Jackson |
| 2009/0287252 A1 | 11/2009 | Marik et al. |
| 2009/0287253 A1 | 11/2009 | Felix et al. |
| 2009/0299411 A1 | 12/2009 | Laskowitz et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0326582 A1 | 12/2009 | Songer et al. |
| 2009/0326583 A1 | 12/2009 | Moumene et al. |
| 2009/0326586 A1 | 12/2009 | Duarte |
| 2010/0004692 A1 | 1/2010 | Biedermann et al. |
| 2010/0004694 A1 | 1/2010 | Little |
| 2010/0004695 A1 | 1/2010 | Stad et al. |
| 2010/0010540 A1 | 1/2010 | Park |
| 2010/0010542 A1 | 1/2010 | Jackson |
| 2010/0010543 A1 | 1/2010 | Jackson |
| 2010/0023061 A1 | 1/2010 | Randol et al. |
| 2010/0030224 A1 | 2/2010 | Winslow et al. |
| 2010/0030272 A1 | 2/2010 | Winslow et al. |
| 2010/0030283 A1 | 2/2010 | King et al. |
| 2010/0036417 A1 | 2/2010 | James et al. |
| 2010/0036422 A1 | 2/2010 | Flynn et al. |
| 2010/0036423 A1 | 2/2010 | Hayes et al. |
| 2010/0036425 A1 | 2/2010 | Barrus et al. |
| 2010/0036432 A1 | 2/2010 | Ely |
| 2010/0036443 A1 | 2/2010 | Hutton et al. |
| 2010/0042149 A1 | 2/2010 | Chao et al. |
| 2010/0042152 A1 | 2/2010 | Semler et al. |
| 2010/0042155 A1 | 2/2010 | Biedermann et al. |
| 2010/0042156 A1 | 2/2010 | Harms et al. |
| 2010/0057125 A1 | 3/2010 | Viker |
| 2010/0057126 A1 | 3/2010 | Hestad |
| 2010/0057131 A1 | 3/2010 | Ely |
| 2010/0063544 A1 | 3/2010 | Butler |
| 2010/0063545 A1 | 3/2010 | Richelsoph |
| 2010/0063546 A1 | 3/2010 | Miller et al. |
| 2010/0063547 A1 | 3/2010 | Morin et al. |
| 2010/0063550 A1 | 3/2010 | Felix et al. |
| 2010/0063552 A1 | 3/2010 | Chin et al. |
| 2010/0069919 A1 | 3/2010 | Carls et al. |
| 2010/0069969 A1 | 3/2010 | Ampuero et al. |
| 2010/0082066 A1 | 4/2010 | Biyani |
| 2010/0087858 A1 | 4/2010 | Abdou |
| 2010/0087862 A1 | 4/2010 | Biedermann et al. |
| 2010/0087863 A1 | 4/2010 | Biedermann et al. |
| 2010/0087864 A1 | 4/2010 | Klein et al. |
| 2010/0087865 A1 | 4/2010 | Biedermann et al. |
| 2010/0094343 A1 | 4/2010 | Pham et al. |
| 2010/0094348 A1 | 4/2010 | Biedermann et al. |
| 2010/0094349 A1 | 4/2010 | Hammer et al. |
| 2010/0094352 A1 | 4/2010 | Iott et al. |
| 2010/0094353 A1 | 4/2010 | Shim et al. |
| 2010/0100136 A1 | 4/2010 | Won et al. |
| 2010/0100137 A1 | 4/2010 | Justis et al. |
| 2010/0106189 A1 | 4/2010 | Miller |
| 2010/0106192 A1 | 4/2010 | Barry |
| 2010/0114165 A1 | 5/2010 | Ely |
| 2010/0114170 A1 | 5/2010 | Barrus et al. |
| 2010/0114171 A1 | 5/2010 | Boachie-Adjei et al. |
| 2010/0114179 A1 | 5/2010 | Moore et al. |
| 2010/0114180 A1 | 5/2010 | Rock et al. |
| 2010/0114182 A1 | 5/2010 | Wilcox et al. |
| 2010/0121386 A1 | 5/2010 | Peultier et al. |
| 2010/0125302 A1 | 5/2010 | Hammill, Sr. et al. |
| 2010/0137908 A1 | 6/2010 | Zhang |
| 2010/0137912 A1 | 6/2010 | Alcock et al. |
| 2010/0137918 A1 | 6/2010 | Wilcox et al. |
| 2010/0137920 A1 | 6/2010 | Hammill, Sr. et al. |
| 2010/0152776 A1 | 6/2010 | Keyer et al. |
| 2010/0152785 A1 | 6/2010 | Forton et al. |
| 2010/0160965 A1 | 6/2010 | Viker |
| 2010/0160967 A1 | 6/2010 | Capozzoli |
| 2010/0160968 A1 | 6/2010 | Joshi et al. |
| 2010/0160974 A1 | 6/2010 | Viker |
| 2010/0160976 A1 | 6/2010 | Biedermann et al. |
| 2010/0168796 A1 | 7/2010 | Eliasen et al. |
| 2010/0168800 A1 | 7/2010 | Biedermann et al. |
| 2010/0168801 A1 | 7/2010 | Biedermann et al. |
| 2010/0168803 A1 | 7/2010 | Hestad et al. |
| 2010/0174322 A1 | 7/2010 | Abdelgany et al. |
| 2010/0179602 A1 | 7/2010 | Dauster et al. |
| 2010/0191293 A1 | 7/2010 | Jackson |
| 2010/0204735 A1 | 8/2010 | Gephart et al. |
| 2010/0211104 A1 | 8/2010 | Moumene et al. |
| 2010/0211105 A1 | 8/2010 | Moumene et al. |
| 2010/0211114 A1 | 8/2010 | Jackson |
| 2010/0222822 A1 | 9/2010 | Farris et al. |
| 2010/0222828 A1 | 9/2010 | Stad et al. |
| 2010/0234902 A1 | 9/2010 | Biedermann et al. |
| 2010/0249843 A1 | 9/2010 | Wegzyn, III |
| 2010/0249846 A1 | 9/2010 | Simonson |
| 2010/0249856 A1 | 9/2010 | Iott et al. |
| 2010/0262185 A1 | 10/2010 | Gelfand et al. |
| 2010/0262187 A1 | 10/2010 | Marik et al. |
| 2010/0262190 A1 | 10/2010 | Ballard et al. |
| 2010/0262191 A1 | 10/2010 | Marik et al. |
| 2010/0262192 A1 | 10/2010 | Foley |
| 2010/0274285 A1 | 10/2010 | Rouleau |
| 2010/0274287 A1 | 10/2010 | Rouleau et al. |
| 2010/0274288 A1 | 10/2010 | Prevost et al. |
| 2010/0298891 A1 | 11/2010 | Jackson |
| 2010/0305621 A1 | 12/2010 | Wang et al. |
| 2010/0312288 A1 | 12/2010 | Hammill, Sr. et al. |
| 2010/0331885 A1 | 12/2010 | Remington et al. |
| 2011/0004256 A1 | 1/2011 | Biedermann et al. |
| 2011/0009906 A1 | 1/2011 | Hestad et al. |
| 2011/0009911 A1 | 1/2011 | Hammill et al. |
| 2011/0029022 A1 | 2/2011 | Zehnder et al. |
| 2011/0040338 A1 | 2/2011 | Jackson |
| 2011/0046683 A1 | 2/2011 | Biedermann et al. |
| 2011/0093015 A1 | 4/2011 | Ramsay et al. |
| 2011/0093021 A1 | 4/2011 | Fanger et al. |
| 2011/0106174 A1 | 5/2011 | Rezach |
| 2011/0106175 A1 | 5/2011 | Rezach |
| 2011/0130792 A1 | 6/2011 | Nydegger et al. |

(56) References Cited

U.S. PATENT DOCUMENTS

| | | |
|---|---|---|
| 2011/0152939 A1 | 6/2011 | Aldridge |
| 2011/0152949 A1 | 6/2011 | Biedermann et al. |
| 2011/0160778 A1 | 6/2011 | Elsbury |
| 2011/0166610 A1 | 7/2011 | Altarac et al. |
| 2011/0178558 A1 | 7/2011 | Barry |
| 2011/0178560 A1 | 7/2011 | Butler et al. |
| 2011/0184469 A1 | 7/2011 | Ballard et al. |
| 2011/0184471 A1 | 7/2011 | Foley et al. |
| 2011/0190822 A1 | 8/2011 | Spitler et al. |
| 2011/0196430 A1 | 8/2011 | Walsh |
| 2011/0202094 A1 | 8/2011 | Pereira et al. |
| 2011/0202095 A1 | 8/2011 | Semler et al. |
| 2011/0230915 A1 | 9/2011 | Anderson et al. |
| 2011/0238119 A1 | 9/2011 | Moumene et al. |
| 2011/0251644 A1 | 10/2011 | Hestad et al. |
| 2011/0257685 A1 | 10/2011 | Hay et al. |
| 2011/0257687 A1 | 10/2011 | Trieu et al. |
| 2011/0257689 A1 | 10/2011 | Fiechter et al. |
| 2011/0257690 A1 | 10/2011 | Rezach |
| 2011/0263945 A1 | 10/2011 | Peterson et al. |
| 2011/0313460 A1 | 12/2011 | Mclean et al. |
| 2011/0313463 A1 | 12/2011 | McLean |
| 2011/0313471 A1 | 12/2011 | McLean et al. |
| 2012/0029568 A1 | 2/2012 | Jackson |
| 2012/0046699 A1 | 2/2012 | Jones et al. |
| 2012/0053636 A1 | 3/2012 | Schmocker |
| 2012/0078307 A1 | 3/2012 | Nihalani |
| 2012/0197314 A1 | 8/2012 | Farris |
| 2012/0232598 A1 | 9/2012 | Hestad et al. |
| 2012/0310284 A1 | 12/2012 | Gerchow |
| 2013/0103097 A1 | 4/2013 | May et al. |

FOREIGN PATENT DOCUMENTS

| | | |
|---|---|---|
| DE | 3630863 | 3/1988 |
| DE | 9202745.8 | 4/1992 |
| DE | 4425392 | 11/1995 |
| DE | 29806563 | 6/1998 |
| DE | 29810798 | 12/1999 |
| DE | 19951145 | 5/2001 |
| DE | 102007055745 | 7/2008 |
| EP | 0195455 | 9/1986 |
| EP | 0172130 | 2/1987 |
| EP | 0276153 | 7/1988 |
| EP | 0667127 | 8/1995 |
| EP | 0669109 | 8/1995 |
| EP | 0677277 | 10/1995 |
| EP | 1277444 | 1/2003 |
| EP | 2082709 | 7/2009 |
| EP | 2468198 | 12/2010 |
| ES | 2384773 | 7/2012 |
| FR | 2467312 | 4/1981 |
| FR | 2715825 | 8/1995 |
| FR | 2717370 | 9/1995 |
| FR | 2718946 | 10/1995 |
| FR | 2799949 | 4/2001 |
| FR | 2814936 | 4/2002 |
| FR | 2815535 | 4/2002 |
| FR | 2856578 | 6/2003 |
| FR | 2865377 | 1/2004 |
| FR | 2846223 | 4/2004 |
| FR | 2857850 | 4/2004 |
| FR | 2925288 | 6/2009 |
| GB | 203508 | 9/1923 |
| GB | 2082709 | 3/1982 |
| GB | 2140523 | 11/1984 |
| GB | 2365345 | 2/2002 |
| GB | 2382304 | 5/2003 |
| JP | S4867159 | 9/1973 |
| JP | S50106061 | 8/1975 |
| JP | H10277070 | 10/1998 |
| JP | 2000325358 | 3/2000 |
| JP | 2002052030 | 2/2002 |
| JP | 2002221218 | 8/2002 |
| SU | 371359 | 2/1973 |
| WO | 8909030 | 10/1989 |
| WO | 8912431 | 12/1989 |
| WO | 9116018 | 10/1991 |
| WO | 9116020 | 10/1991 |
| WO | 9203100 | 3/1992 |
| WO | 9321848 | 11/1993 |
| WO | 9325161 | 12/1993 |
| WO | 9410927 | 5/1994 |
| WO | 9410944 | 5/1994 |
| WO | 9426191 | 11/1994 |
| WO | 9428824 | 12/1994 |
| WO | 9501132 | 1/1995 |
| WO | 9513755 | 5/1995 |
| WO | 9528889 | 11/1995 |
| WO | 9531947 | 11/1995 |
| WO | 9535067 | 12/1995 |
| WO | 9606576 | 3/1996 |
| WO | 9621396 | 7/1996 |
| WO | 9625104 | 8/1996 |
| WO | 9628105 | 9/1996 |
| WO | 9628118 | 9/1996 |
| WO | 9641582 | 12/1996 |
| WO | 9714366 | 4/1997 |
| WO | 9714368 | 4/1997 |
| WO | 9727812 | 8/1997 |
| WO | 9730649 | 8/1997 |
| WO | 9737604 | 10/1997 |
| WO | 9737605 | 10/1997 |
| WO | 9812977 | 4/1998 |
| WO | 9815233 | 4/1998 |
| WO | 9825534 | 6/1998 |
| WO | 9832386 | 7/1998 |
| WO | 9834554 | 8/1998 |
| WO | 9834556 | 8/1998 |
| WO | 9838924 | 9/1998 |
| WO | 9903415 | 1/1999 |
| WO | 9905980 | 2/1999 |
| WO | 9932084 | 7/1999 |
| WO | 9938463 | 8/1999 |
| WO | 9947083 | 9/1999 |
| WO | 9949802 | 10/1999 |
| WO | 2000015125 | 3/2000 |
| WO | 2000022997 | 4/2000 |
| WO | 2000027297 | 5/2000 |
| WO | 2000072769 | 7/2000 |
| WO | 2000065268 | 11/2000 |
| WO | 2000066045 | 11/2000 |
| WO | 2001006940 | 2/2001 |
| WO | 2001008574 | 2/2001 |
| WO | 2001010317 | 2/2001 |
| WO | 2001015612 | 3/2001 |
| WO | 2001022893 | 4/2001 |
| WO | 2001028435 | 4/2001 |
| WO | 2001028436 | 4/2001 |
| WO | 2001045576 | 6/2001 |
| WO | 2001049191 | 7/2001 |
| WO | 20010058370 | 8/2001 |
| WO | 2001067972 | 9/2001 |
| WO | 2001067974 | 9/2001 |
| WO | 2002022030 | 3/2002 |
| WO | 2002034150 | 5/2002 |
| WO | 2002054966 | 7/2002 |
| WO | 2002102259 | 12/2002 |
| WO | 2003007828 | 1/2003 |
| WO | 2003026523 | 4/2003 |
| WO | 2003037199 | 5/2003 |
| WO | 2003047442 | 6/2003 |
| WO | 2003068083 | 8/2003 |
| WO | 2003068088 | 8/2003 |
| WO | 2003084415 | 10/2003 |
| WO | 2003094699 | 11/2003 |
| WO | 2004021900 | 3/2004 |
| WO | 2004022108 | 3/2004 |
| WO | 2004041100 | 5/2004 |
| WO | 2004075778 | 9/2004 |
| WO | 2004089245 | 10/2004 |
| WO | 2004098452 | 11/2004 |
| WO | 2004105577 | 12/2004 |
| WO | 2004107997 | 12/2004 |

(56) References Cited

FOREIGN PATENT DOCUMENTS

| | | |
|---|---|---|
| WO | 2005000136 | 1/2005 |
| WO | 2005000137 | 1/2005 |
| WO | 2005013839 | 2/2005 |
| WO | 2005018466 | 3/2005 |
| WO | 2005018471 | 3/2005 |
| WO | 2005020829 | 3/2005 |
| WO | 2005030068 | 4/2005 |
| WO | 2005065374 | 7/2005 |
| WO | 2005072632 | 8/2005 |
| WO | 2005082262 | 9/2005 |
| WO | 2005087121 | 9/2005 |
| WO | 2005099400 | 10/2005 |
| WO | 2005102195 | 11/2005 |
| WO | 2005104969 | 11/2005 |
| WO | 2006005198 | 1/2006 |
| WO | 2006017616 | 2/2006 |
| WO | 2006020530 | 2/2006 |
| WO | 2006042188 | 4/2006 |
| WO | 2006047711 | 5/2006 |
| WO | 2006054111 | 5/2006 |
| WO | 2006065607 | 6/2006 |
| WO | 2006066685 | 6/2006 |
| WO | 2006068711 | 6/2006 |
| WO | 2006071742 | 7/2006 |
| WO | 2006079531 | 8/2006 |
| WO | 2006096240 | 9/2006 |
| WO | 2006096351 | 9/2006 |
| WO | 2006104874 | 10/2006 |
| WO | 2006110463 | 10/2006 |
| WO | 2006116437 | 11/2006 |
| WO | 2006119447 | 11/2006 |
| WO | 2007002409 | 1/2007 |
| WO | 2007038350 | 4/2007 |
| WO | 2007040750 | 4/2007 |
| WO | 2007040888 | 4/2007 |
| WO | 2007041702 | 4/2007 |
| WO | 2007053566 | 5/2007 |
| WO | 2007060534 | 5/2007 |
| WO | 2007075454 | 7/2007 |
| WO | 2007081849 | 8/2007 |
| WO | 2007087469 | 8/2007 |
| WO | 2007087628 | 8/2007 |
| WO | 2007090021 | 8/2007 |
| WO | 2007092056 | 8/2007 |
| WO | 2007092870 | 8/2007 |
| WO | 2007097905 | 8/2007 |
| WO | 2007109470 | 9/2007 |
| WO | 2007114834 | 10/2007 |
| WO | 2007118045 | 10/2007 |
| WO | 2007121030 | 10/2007 |
| WO | 2007121057 | 10/2007 |
| WO | 2007121271 | 10/2007 |
| WO | 2007123920 | 11/2007 |
| WO | 2007124222 | 11/2007 |
| WO | 2007124249 | 11/2007 |
| WO | 2007127595 | 11/2007 |
| WO | 2007127604 | 11/2007 |
| WO | 2007130835 | 11/2007 |
| WO | 2007130840 | 11/2007 |
| WO | 2007130941 | 11/2007 |
| WO | 2007138270 | 12/2007 |
| WO | 2007146032 | 12/2007 |
| WO | 2008005740 | 1/2008 |
| WO | 2008006098 | 1/2008 |
| WO | 2008008511 | 1/2008 |
| WO | 2008013892 | 1/2008 |
| WO | 2008027860 | 3/2008 |
| WO | 2008033742 | 3/2008 |
| WO | 2008036975 | 3/2008 |
| WO | 2008037256 | 4/2008 |
| WO | 2008039777 | 4/2008 |
| WO | 2008042948 | 4/2008 |
| WO | 2008048923 | 4/2008 |
| WO | 2008048953 | 4/2008 |
| WO | 2008051737 | 4/2008 |
| WO | 2008069420 | 6/2008 |
| WO | 2008070716 | 6/2008 |
| WO | 2008134703 | 6/2008 |
| WO | 2008078163 | 7/2008 |
| WO | 2008082737 | 7/2008 |
| WO | 2008100590 | 8/2008 |
| WO | 2008118295 | 10/2008 |
| WO | 2008119006 | 10/2008 |
| WO | 2008124772 | 10/2008 |
| WO | 2008140756 | 11/2008 |
| WO | 2008157589 | 12/2008 |
| WO | 2009003153 | 12/2008 |
| WO | 2009006225 | 1/2009 |
| WO | 2009011845 | 1/2009 |
| WO | 2009014540 | 1/2009 |
| WO | 2009015100 | 1/2009 |
| WO | 2009018086 | 2/2009 |
| WO | 2009029928 | 3/2009 |
| WO | 2009055028 | 4/2009 |
| WO | 2009055400 | 4/2009 |
| WO | 2009055407 | 4/2009 |
| WO | 2009152302 | 12/2009 |
| WO | 2009155360 | 12/2009 |
| WO | 2010017631 | 2/2010 |
| WO | 2010018316 | 2/2010 |
| WO | 2010018317 | 2/2010 |
| WO | 2010019857 | 2/2010 |
| WO | 2010030916 | 3/2010 |
| WO | 2010045383 | 4/2010 |
| WO | 2010065648 | 6/2010 |
| WO | 2010078901 | 7/2010 |
| WO | 2010111500 | 9/2010 |
| WO | 2010120989 | 10/2010 |
| WO | 2010147639 | 12/2010 |
| WO | 2011043805 | 4/2011 |
| WO | 2011068818 | 6/2011 |
| WO | 2012033532 | 3/2012 |
| WO | 2012075827 | 6/2012 |
| WO | 2012088890 | 7/2012 |

OTHER PUBLICATIONS

CD Horizon M8 Multi Axial Screw Spinal System Brochure, Medtronic Sofamor Danek, no publish date.
Claris Instrumentation Brochure, G Med, pub. 1997.
Contour Spinal System Brochure, Ortho Development, no publish date.
EBI Omega 21 Brochure, EBI Spine Systems, pub. 1999.
SDRS Surgical Dynamics Rod System Brochure, Surgical Dynamics, pub. 1998-99.
Silhouette Spinal Fixation System Brochure, Sulzer Medica Spine-Tech, no publish date.
Spine, Lipcott, Williams & Wilkins, Inc. vol. 24, No. 15, p. 1495.
The Moss Miami 6.0mm System Advertisement, author unknown, no publish date.
The Rod Plate System Brochure, Stryker Howmedica Osteonics, pub. Oct. 1999.
The Strength of Innovation Advertisement, Blackstone Medical Inc., no publish date.
Versalok Low Back Fixation System Brochure, Wright Medical Technology, Inc., pub. 1997.
VLS System Variable Locking Screw Brochure, Interpore Cross International, 1999.
Xia Spinal System Brochure, Stryker Howmedica Osteonics, no publish date.
Brochure of DePuySpine on Surgical Technique, Published 2004, pp. 1-36.

\* cited by examiner

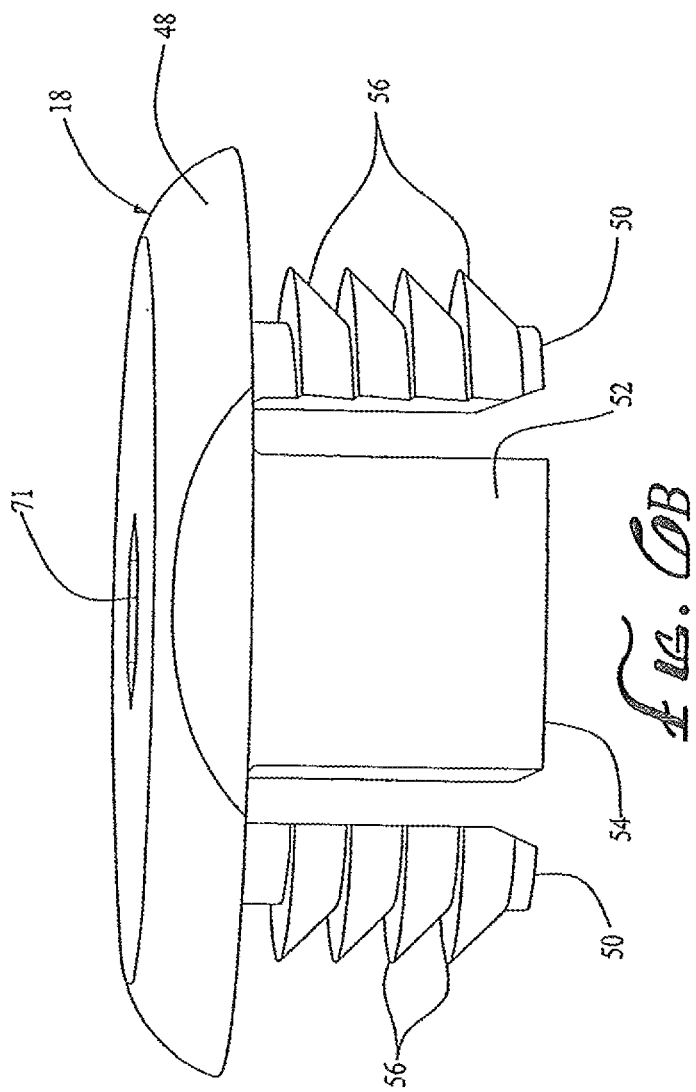

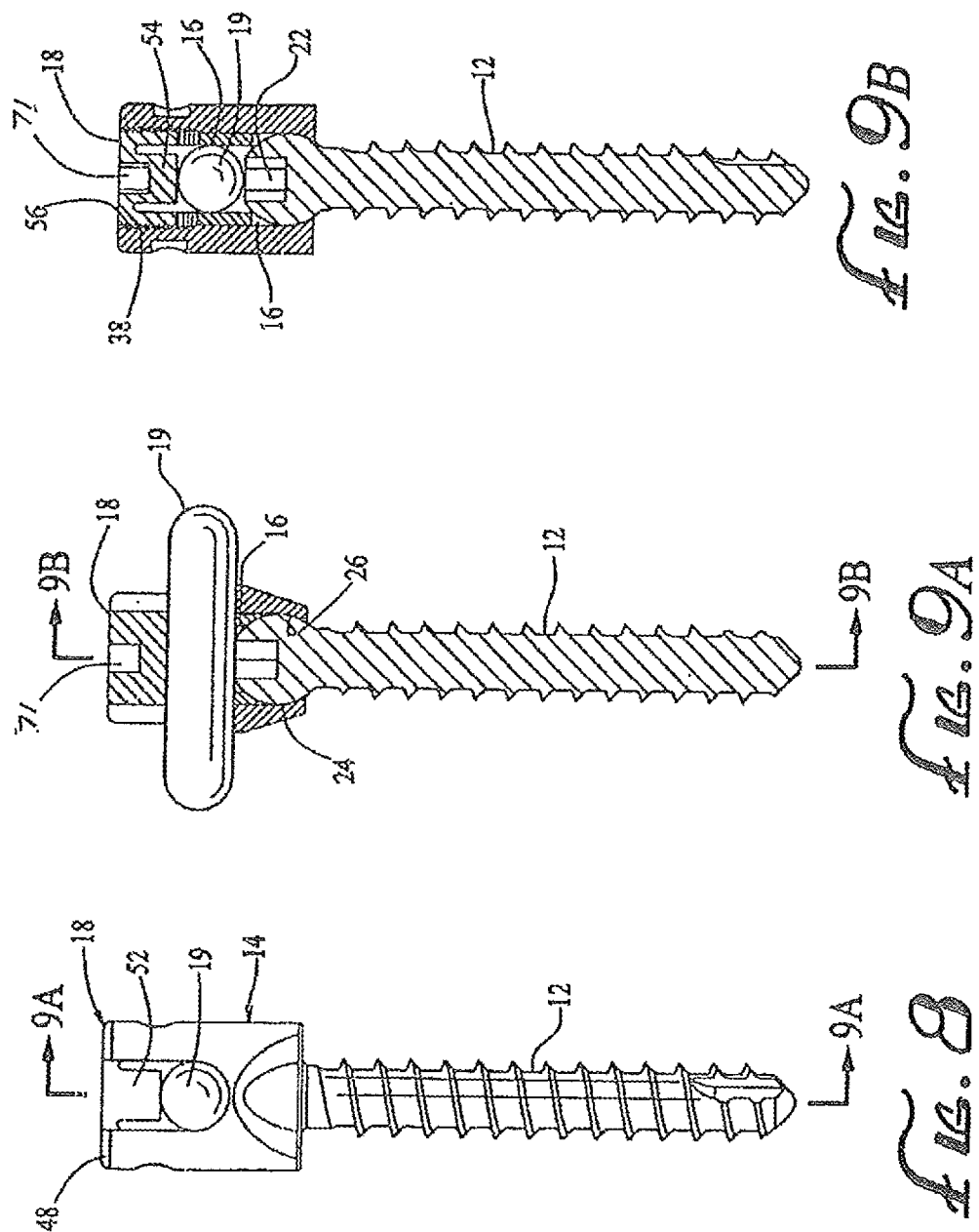

PIVOTAL BONE ANCHOR ASSEMBLY WITH BIASED BUSHING FOR PRE-LOCK FRICTION FIT

CROSS-REFERENCE TO RELATED APPLICATIONS

This application is a Continuation of U.S. patent application Ser. No. 13/507,857, filed Aug. 2, 2012, now U.S. Pat. No. 8,636,775, which was a Continuation of U.S. patent application Ser. No. 12/154,448, filed May 23, 2008, now U.S. Pat. No. 8,298,265, that was a continuation of U.S. patent application Ser. No. 10/848,946, filed May 19, 2004, now U.S. Pat. No. 7,377,923 that claimed the benefit of U.S. Provisional Application No. 60/472,578, filed May 22, 2003 and U.S. Provisional Application No. 60/527,060, filed Dec. 4, 2003, all of which are incorporated by reference herein.

BACKGROUND OF THE INVENTION

The present invention relates generally to an apparatus for internal fixation of the spine and, more specifically to a novel locking mechanism for a variable angle spinal screw assembly that provides for easier implantation, a wide range of motion, ease of disassembly for adjustment or replacement of the stabilization rod and eliminates conventional threaded engagements and the crossover threading, torquing and other problems associated therewith.

Certain spinal conditions, including a fracture of a vertebra and a herniated disc, indicate treatment by spinal immobilization. Several methods of spinal joint immobilization are known, including surgical fusion and the attachment of pins and bone plates to the affected vertebras. One known device is a bone interface anchor inserted into at least two spaced-apart vertebras, with a stabilization rod interconnecting the two or more anchors to stabilize the vertebras spanned by the anchors. Specifically, a bone screw is received within a socket formed in the anchor. The anchor further includes a channel, extending perpendicular to the longitudinal axis of the bone screw, for receiving the stabilization rod. The anchor further comprises a threaded portion above the channel. After the bone screw and anchor have been inserted into the bone material, the rod is placed within the channel and a nut is mated with the external threads of the anchor. The nut applies a compressive force between the rod and the screw head to firmly fix the rod between the spanned vertebras and thus stabilize the spinal vertebrae.

During surgical implantation of these prior art stabilization systems, the surgical site is crowded with tissue masses, sponges and other surgical implements that obstruct access to the anchor threads. Given the difficult access, it is possible for the surgeon to cross-thread the nut with the threads of the anchor after the fixation rod is in place. If the threads of the anchor are cross-threaded, the cross-threaded coupling must be removed and replaced before the surgery can proceed. In addition, the threaded fastener (e.g., the nut) is frequently removed and then reinstalled as the surgeon makes progressive bends to contour the fixation rod. This increases the surgery with each on-off iteration and further increases the chances of cross-threading.

Another problem associated with threaded attachments is the torque exerted on the anchor during the tightening of the threaded fastener about the upper end portion of the fixation device. This torque can inadvertently introduce stress points along the rod, bend the rod or even loosen the threaded engagement of the anchor in the bone. The elimination of the conventional threaded attachments in the fixation device of the present invention also obviates these problems associated with torquing.

The angle at which the anchor screws extend from the vertebra pedicle is dictated by the spinal curvature, the orientation of individual vertebra within the spine, and the surgeon's placement of the screw within the pedicle. For example, there is considerable spinal curvature in the region of the S1-L5 vertebra junction and the angle between the longitudinal axis of the screws and the vertebra in that region vary over a wide range. Also, it may be necessary to displace one or more of the anchors from the spin midline to effectuate maximum spinal stabilization. Thus, the rod-receiving channels are typically not collinear nor coplanar and, the rod must be shaped or contoured by the surgeon during the implantation procedure to fit within the channels along the spinal column. The prior art systems allow the coupling unit to pivot with respect to the screw over a range of about .+-.20.degree. to .+-.30.degree., providing some margin for the surgeon to place the rod within the channel.

One challenge with current variable angle or polyaxial systems is aligning the coupling units in a manner that minimizes pre-insertion rod contouring while allowing the surgeon maximum range to optimize pedicle screw placement. This is especially challenging when fusing the S1-L5 junction. The prior art coupling units allow only a limited range of motion with respect to the screw head. The present invention allows a first range of motion in all directions, but also provides an extended range of motion in the medial--lateral--inferior direction (head-to-toe). This extended range of motion, as compared to the prior art, allows the surgeon additional freedom in locating the screws and eases the assembly process by reducing the requirement for rod contouring.

Thus, the present invention provides an extended range of motion as compared to the prior art, allowing the surgeon additional freedom in locating the screws and easing the assembly process by reducing the requirements for rod contouring. The present invention additionally eliminates the numerous problems heretofore experienced with threaded fasteners. The result is a significantly improved variable angle spinal screw assembly.

SUMMARY OF THE INVENTION

Briefly, the present invention comprises a variable angle spinal screw assembly for providing an adjustable securement of a stabilization rod between at least two spaced-apart vertebrae to effect internal fixation of the spine across the affected vertebrae. The assembly is used with at least one other such assembly to secure the fixation rod and includes a pedicle screw, a body member and a locking cap. The pedicle screw has a substantially spherical head portion defining a slot therein used to drive the screw into a vertebrae. The body member is generally cylindrical in configuration and is adapted to receive the head portion of the pedicle screw and cooperate therewith so as to define a modified ball joint to allow variable angular movement of the body member with respect to the pedicle screw with the threaded shaft portion of the screw extending through an opening in the inner end of the body member (or lower end as seen from the perspective shown in the drawings). The body member additionally defines a pair of opposed parallel slots axially disposed in the side wall thereof to receive a portion of the cylindrical fixation rod. The interior walls of the upper portion of the body member are provided with serrations defining a plurality of axially aligned ratchet teeth. The ratchet teeth are adapted to cooperate with opposed mating teeth formed on the outer surface of a locking cap such that upon pressing the locking cap downwardly within the body member of the assembly against the fixation rod and the rod against the head of the pedicle screw, the interlocking teeth will hold the cap in place and secure the fixation rod in place within the assembly. By rotating the locking cap with respect to the body member, the ratchet teeth are disengaged, relieving the pressure of the cap on the fixation rod and thus releasing the securement of the rod.

By providing the body member of the assembly with a rounded interior surface about the lower opening therein that mates with the rounded lower surface of the spherical screw head and with concave exterior surfaces on the underside of the body member about said opening, the angular orientation of the central axis of the body member relative to the pedicle screw is widely variable, providing an extended range of motion to facilitate surgical installation. Through the cooperation of the interlocking ratchet teeth on the body member and locking cap, installation is further facilitated and the disadvantages of conventional threaded fasteners are obviated.

In preferred embodiments of the present invention, a bushing is employed within the body member to better distribute the longitudinal forces exerted on the pedicle screw. The bushing can be of a generally cylindrical configuration, positioned adjacent the interior side wall of the body member and defines a seat for the fixation rod and a bifurcated depending skirt that abuts and mates with portions of the head of the pedicle screw upon being urged thereagainst by the locking cap pressing downwardly on the fixation rod. As a result, the force exerted on the screw is distributed about the head of the screw to improve the locking securement between the screw and the body member.

In addition, by providing a keyed interface between the pedicle screw head and the body member, the pedicle screw can be inserted into the bone by the surgeon unencumbered by the body member. The body member can then be aligned with the head of the embedded screw, slid onto and over the screw head, reoriented so as to mate the inner lower surface of the body member with the screw head to define the above-described modified ball joint and the resulting variable angle or polyaxial relationship. Such a keyed interface can be provided by a threaded engagement between the lower end of the body member and fixed screw head by which the body member can be screwed onto and over the head of the embedded screw. Alternatively, the screw head and body member opening can be multi-sided and configured so as to allow the body member to be slid over the screw head only when the two components are in a given alignment. Once the body member is slid over the head and rotated so as to misalign the respective sides, the body member is locked onto the screw head and the variable angle mating relationship therebetween is formed.

It is the principal object of the present invention to provide an improved securement of a fixation rod between two or more spaced-apart vertebrae to effect internal fixation of the spine across the affected vertebrae.

This and other objects and advantages of the present invention will be readily apparent from the following detailed description taken in conjunction with the accompanying drawings.

BRIEF DESCRIPTION OF THE DRAWINGS

FIGS. 6A and 6B are perspective views of a first embodiment of the cap of the present invention.

FIG. 8 is a side view of the variable angle spinal screw assembly of the present invention.

FIG. 9A is a sectional view taken along the line A-A of FIG. 8

FIG. 9B is a sectional view taken along the line B-B of FIG. 8.

DETAILED DESCRIPTION OF THE PREFERRED EMBODIMENT

Figure 1:
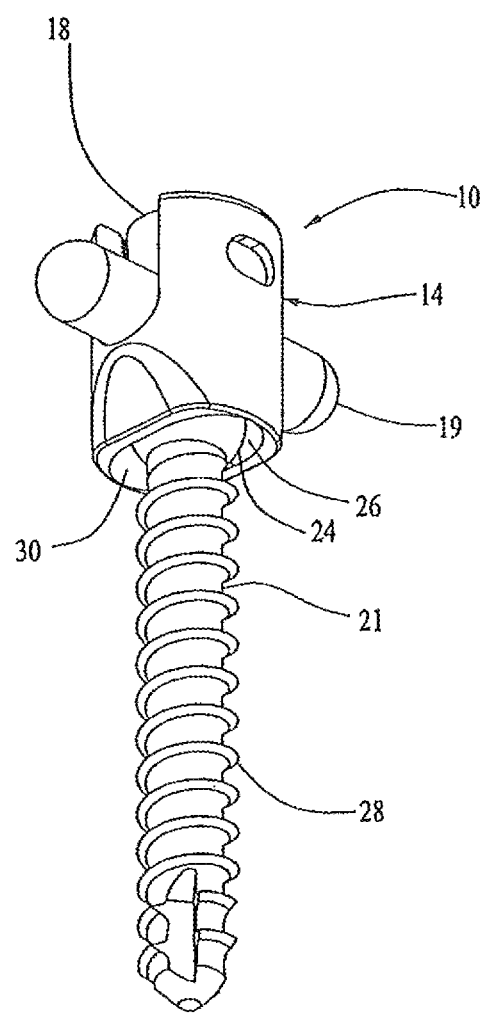
FIG. 1 is a perspective view of the variable angle spinal screw assembly of the present invention.
Figure 2:
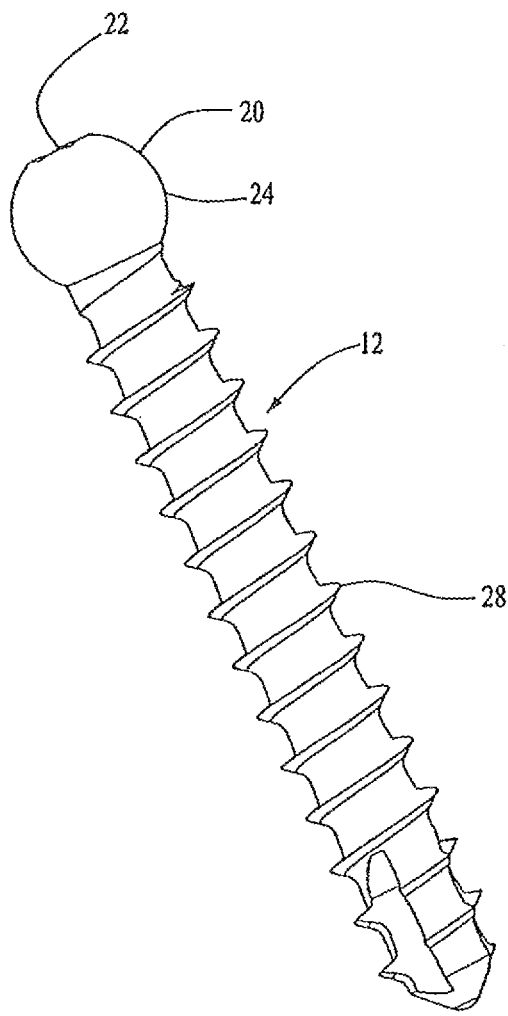
FIG. 2 is a perspective view of the bone screw portion of the assembly of the present invention.

Referring now in detail to the drawings, the variable angle spinal screw assembly 10 of the present invention comprises a pedicle screw 12, a body member 14, a bushing 16 and a locking cap 18. The assembly 10 is used with at least one other such assembly and a stabilization or fixation rod 19 to connect the assemblies and stabilize the vertebras into which the assemblies are inserted. The pedicle screw 12 preferably employed in assembly 10 has a spherical head 20 defining a slot 22 therein used to drive the screw into the bone. The rounded surface 24 defined by the lower portion of screw head 20 rests upon and mates with a rounded interior surface 26 formed in the inner or lower end of the body member 14 of the assembly 10 so as to form a modified ball joint that provides the desired variable angular movement of the body member with respect to the embedded pedicle screw. The threaded shaft portion 28 of screw 12 extends therefrom through the opening 30 in the lower end of body member 14.

The body member 14 of assembly 10 further defines a pair of opposed parallel slots 32 axially disposed in the side wall 34 thereof, which terminate at their lower ends in curvilinear surfaces 36. The two slots 32 are sized to receive the fixation rod therein as shown in the drawings with the walls 35 defining the slots preferably extending upwardly beyond the midpoint of the rod and can be inclined slightly to provide a slight holding force on the rod prior to securing the rod with the locking cap 18. Thus, during assembly, the surgeon exerts a slight downward force on the rod, snapping the rod into the transverse channel defined by the aligned slots 32.

The outer or upper interior surface of side walls 34 of the body member 14 both have radially projecting serrations formed therein defining a plurality of axially aligned ratchet teeth 38. The exterior bottom surface 40 of body member 14 has spaced outwardly extending concave surface 42 formed therein and a pair of perpendicularly disposed concave surfaces 44. Surfaces 42 and 44, together with mating surfaces 24 and 26 on the screw head and body member of the assembly, provide an extended range of motion of the body member 14 with respect to the pedicle screw 12. In one embodiment, the range of motion is about .+-.30.degree. in all directions (as measured from the longitudinal axis of the screw) and about .+-.40.degree. in the inferior-superior direction, the outwardly (as viewed from the screw head) concave surfaces provide the .+-.40.degree. range of motion, for a total motion range of 80.degree.. This extended range of motion, as compared to the prior art, allows the surgeon additional freedom in locating the screws and eases the assembly process by reducing the requirement for a rod contouring.

Figure 3A:
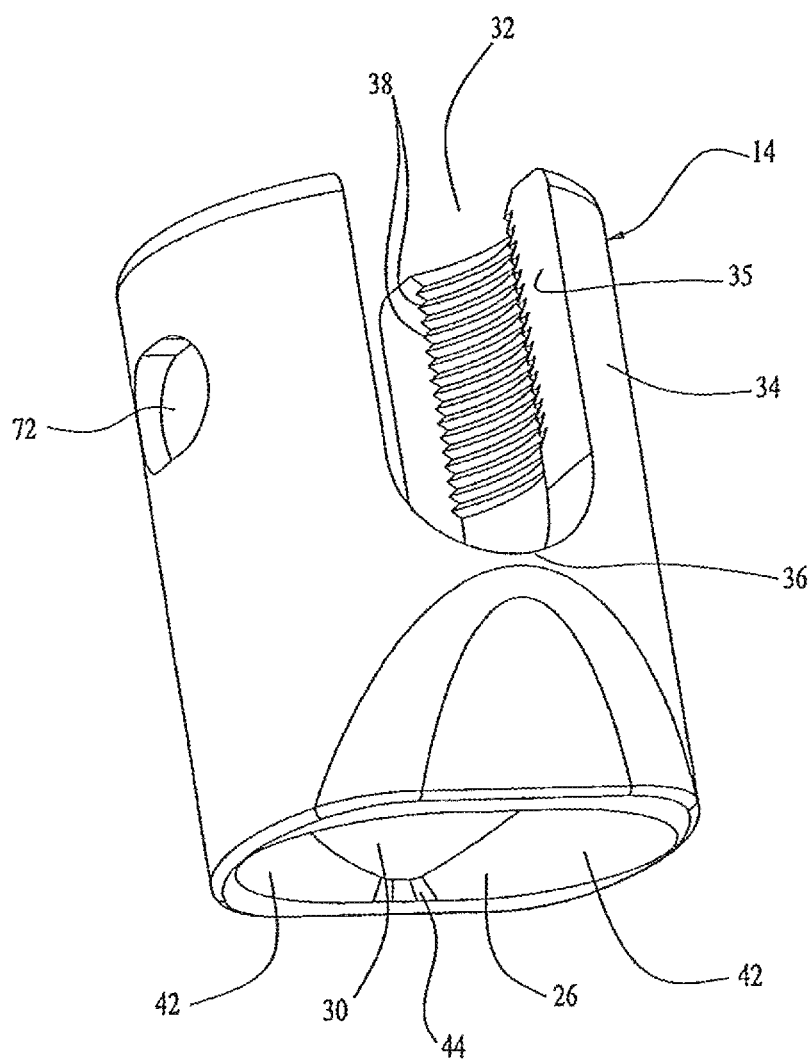
FIGS. 3A and 3B are perspective views of the body member of the assembly of the present invention.
Figure 3B:
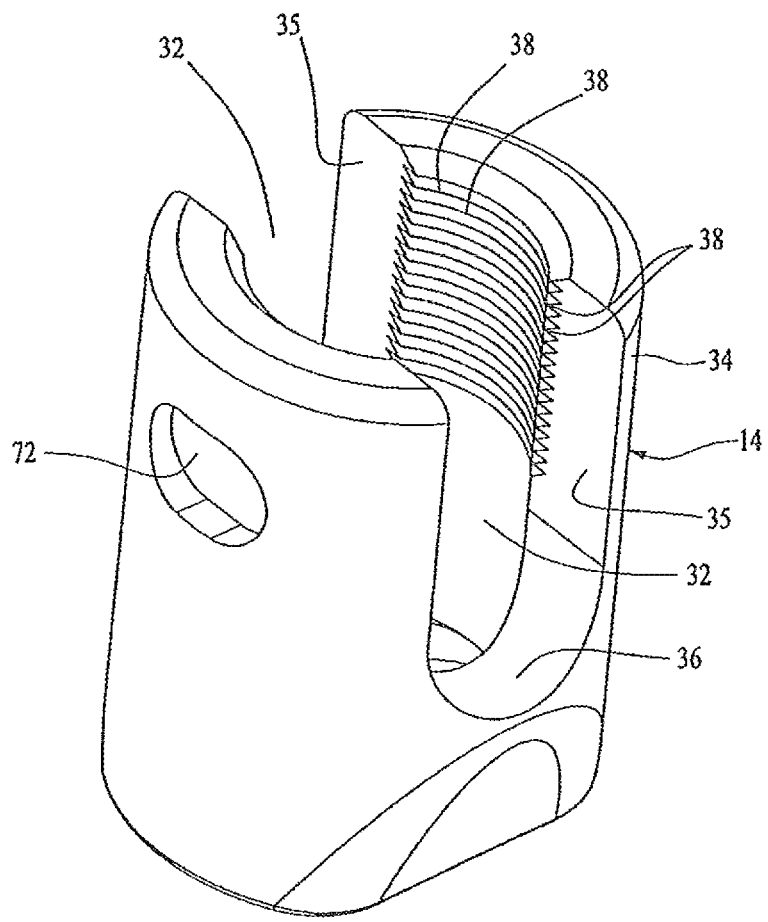
Figure 4:
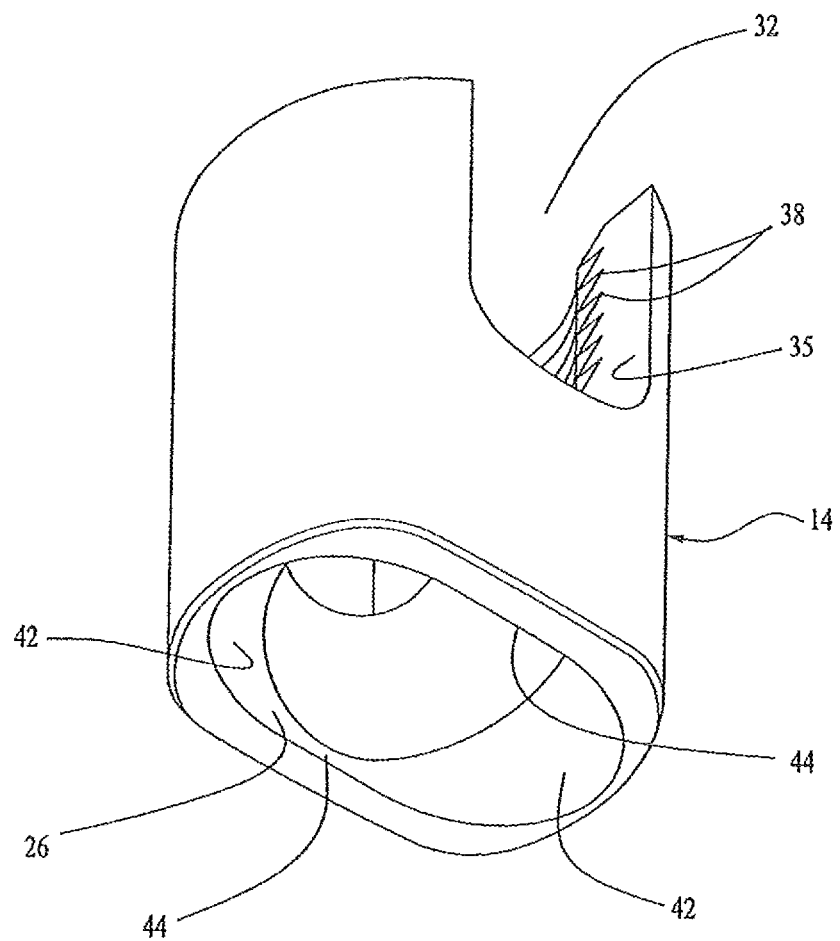
FIG. 4 is another perspective view of the body member of the present invention showing the lower surface thereof.
Figure 5:
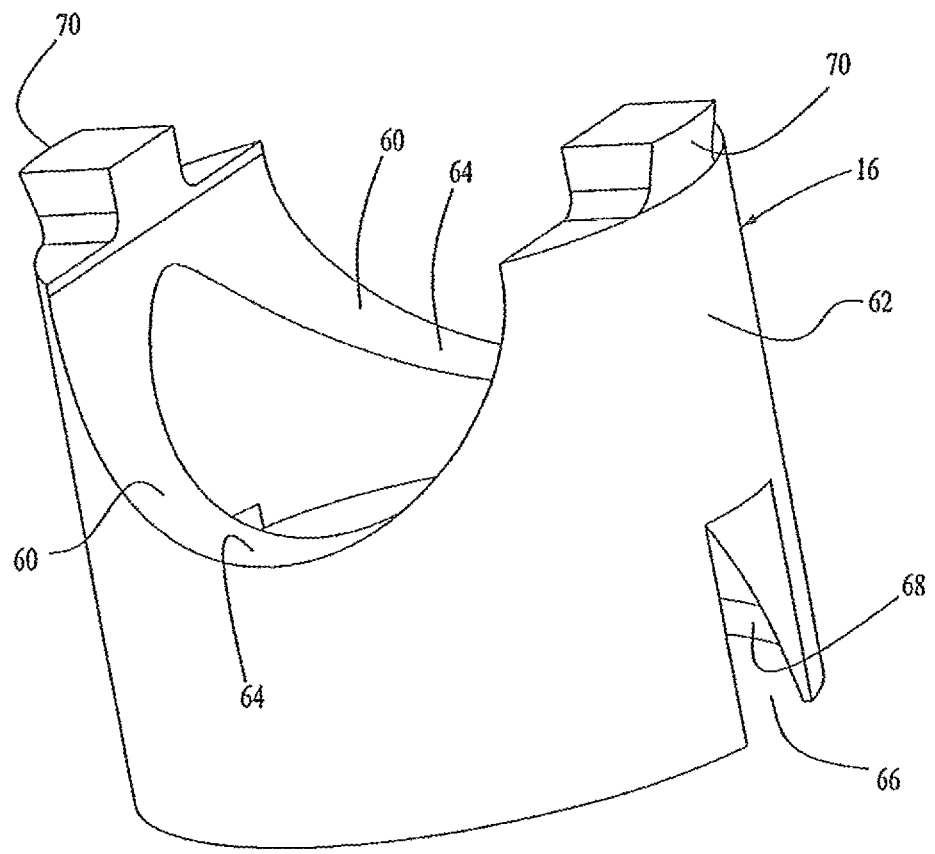
FIG. 5 is a perspective view of the bushing employed in the present invention.
Figure 6A:
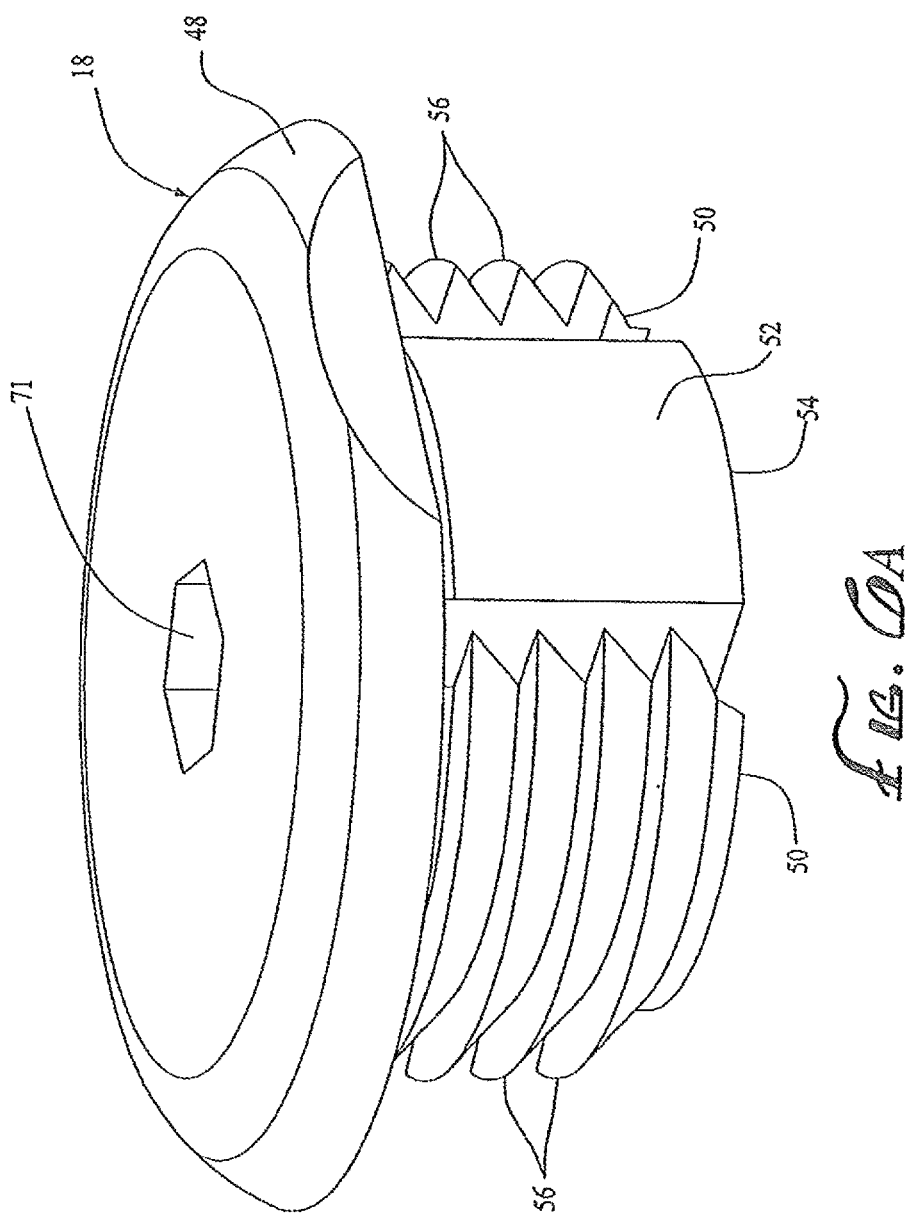

To secure the fixation rod 19 within the body member 14 of the assembly, locking cap 18 is provided. Cap 18 defines a top portion 48, a pair of opposed arcuate depending leg portions 50 and a centrally disposed depending projection 52 equidistantly spaced from leg portions 50. Central projection 52 preferably defines a planar lower or bottom surface 54. The leg portions 50 of cap 18 each have a plurality of radially projecting serrations formed therein that define a plurality of axially aligned ratchet teeth 56 adopted to engage teeth 38 on the opposed interior side walls 34 of the body member 14, as will be described A bushing 16 is preferably employed within the body member 14 of the assembly 10 adjacent side walls 34 to better distribute the longitudinal forces exerted on the pedicle screw. Bushing 16 defines a pair of opposed concave surfaces 60 formed in the upper end of a circular skirt 62 so as to define a seat 64 for the fixation rod 19. The lower portion of bushing skirt 62 is slotted at 66 to provide flexibility therein and defines depending tapered end surfaces 68 adapted to abut opposed sides of the rounded screw head 20. A pair of outwardly projecting opposed resilient tabs 70 are provided at the upper ends of the bushing 16 between concave surfaces 60 that in some embodiments are adapted to be received in a snap fitment within a pair of opposed apertures (not shown) formed in the side wall 34 of body member 14 whereupon the rod seat 64 in bushing 16 is aligned with the channel in the body member. Note that in the illustrated embodiment shown in FIG. 3B, for example, the resilient tabs 70 will engage with the body member 14 inner cylindrical surface located below the ratchet teeth 38, the illustrated aperture 72 being located in the vicinity of the ratchet teeth 38 that cooperate with the locking cap 18 and thus at a distance from the bushing 16. Note that only one of apertures 72 is illustrated in FIGS. 3A and 3B to better illustrate the configuration of the ratchet teeth 38. In an alternative embodiment, the tabs could be removed from the bushing 16 and located on the body member 14 for engagement with apertures or other receiving structure or members formed in opposed sides of the bushing.

To provide a basic stability to the system during initial assembly, the bushing 16 with its slotted lower skirt portion can be configured to provide a press fitment about the screw head 20 so that the pedicle screw 12, body member 14 and bushing 16 will not move freely prior to the insertion and securement of the fixation rod. In addition, the upper portion of the bushing could be configured such that the wall surfaces 60 defining the rod seat 64 therein extend upwardly past the midpoint of the rod and are slightly inwardly inclined. This would provide the same slight holding force when the rod is pushed into the bushing seat 64 that was above described with reference to the channel walls 35 in the body member 14 of the assembly 10.

Upon securing the bushing 16 in the body member 14 and the fixation rod 12 in bushing seat 64, the locking cap 18 is positioned such that the depending leg portions 50 thereon are aligned with the side walls 34 of body member 14. Upon pressing the cap 18 downwardly into body member 14, the ratchet teeth 38 and 56 on the assembly body and cap interlock so as to allow the cap to be pressed downwardly but not retracted. As cap 18 is pressed downwardly into the body member of the assembly, the planar bottom surface 54 of the central projection 52 thereon abuts the fixation rod 19 and presses the rod into and against the seat 64 formed on the upper end of bushing 16. The resulting pressure on the bushing causes the tapered surfaces 68 on the lower end of the bushing to press against the rounded surface of the screw head 20, thereby securing the rod in seat 64 and providing a decentralized and evenly distributed force acting along the longitudinal axis of the screw. Thus, the use of bushing 16 creates a taper lock between the pedicle screw and body member and increases the area of contact therebetween. The result is an improved locking securement over that provided by the earlier described direct contact of the fixation rod against the upper end of the screw head.

The interlocked ratchet teeth will allow the surgeon to tighten the clamping force on the fixation rod by simply pressing downwardly on the locking cap 18. The teeth will hold the component parts in place. To adjust or remove the rod 19, the locking cap 18 is simply rotated 90 degrees about its longitudinal axis, whereupon the teeth 38 on the depending leg portions 50 of the cap are aligned with the open slots 32 in the body member 14, allowing the cap to be simply pulled upwardly away from the fixation rod 19. A hexagonally configured slot 71 is provided in the top portion 48 of cap 18 to facilitate the rotation of the locking cap with a suitably sized mating tool.

In use, at least two of the pedicle screws 12 with the body members 14 and attached bushings 16 disposed about the screw are inserted into the vertebra pedicles spanning the vertebra to be fixated. The surgeon preliminary contours the fixation rod and checks the alignment between the rod and the mating channels formed by the slots in the bushing and body member of the assemblies. Since additional contouring is usually required to improve the alignment, the surgeon incrementally adjusts the rod shape and checks the fit within the channels until the rod properly fits in all channels. During the contouring process, a locking cap 18 can be mated with one or more of the body member 14 (by pressing the cap axially into the body member to create the interlock between the ratchet teeth on the body member and the cap) to temporarily hold the rod in place, thereby assisting the surgeon in achieving an accurate fit. The locking caps are then easily removable (by rotating the cap a quarter of a turn to disengage the interlocking teeth), allowing the rod to be further contoured. Once properly contoured, the rod is inserted into the channels and a locking cap is pressed tightly into each body member and bushing to secure the rod in place. To effect securement of the rod at each of the pedicle screw assemblies, it is solely necessary to press the locking cap longitudinally into the body member such that the bottom surface 54 of the central projection 52 on the cap presses against the fixation rod 19, causing the rod to press downwardly against the bushing 16, which in turn mates with and presses against the head of the pedicle screw.

Figure 10:
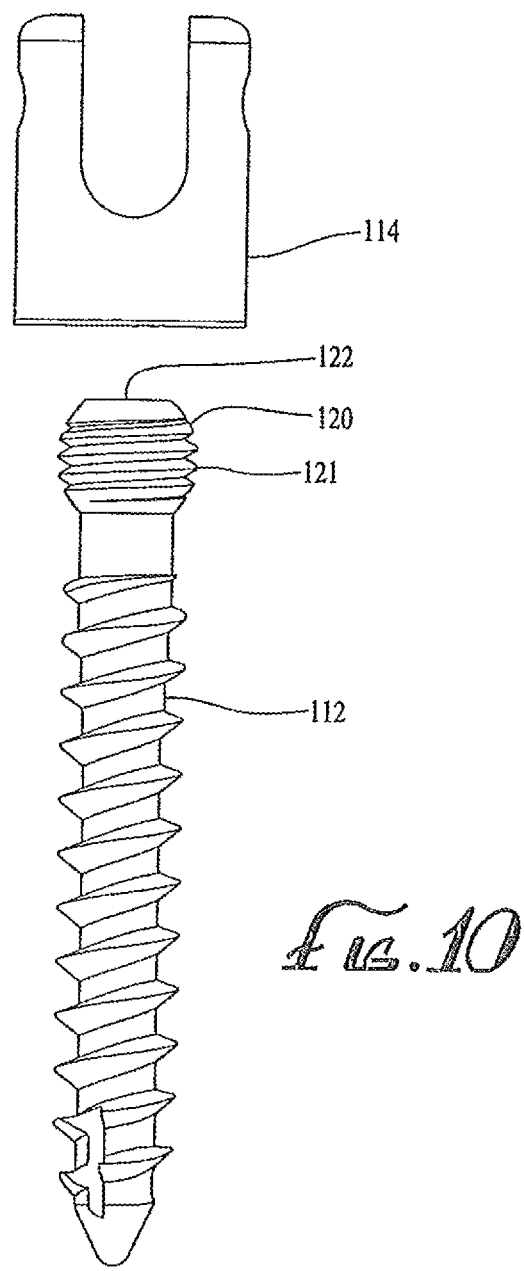
FIG. 10 is an exploded view of a modified form of the pedicle screw and body member employed in the present invention.
Figure 11:
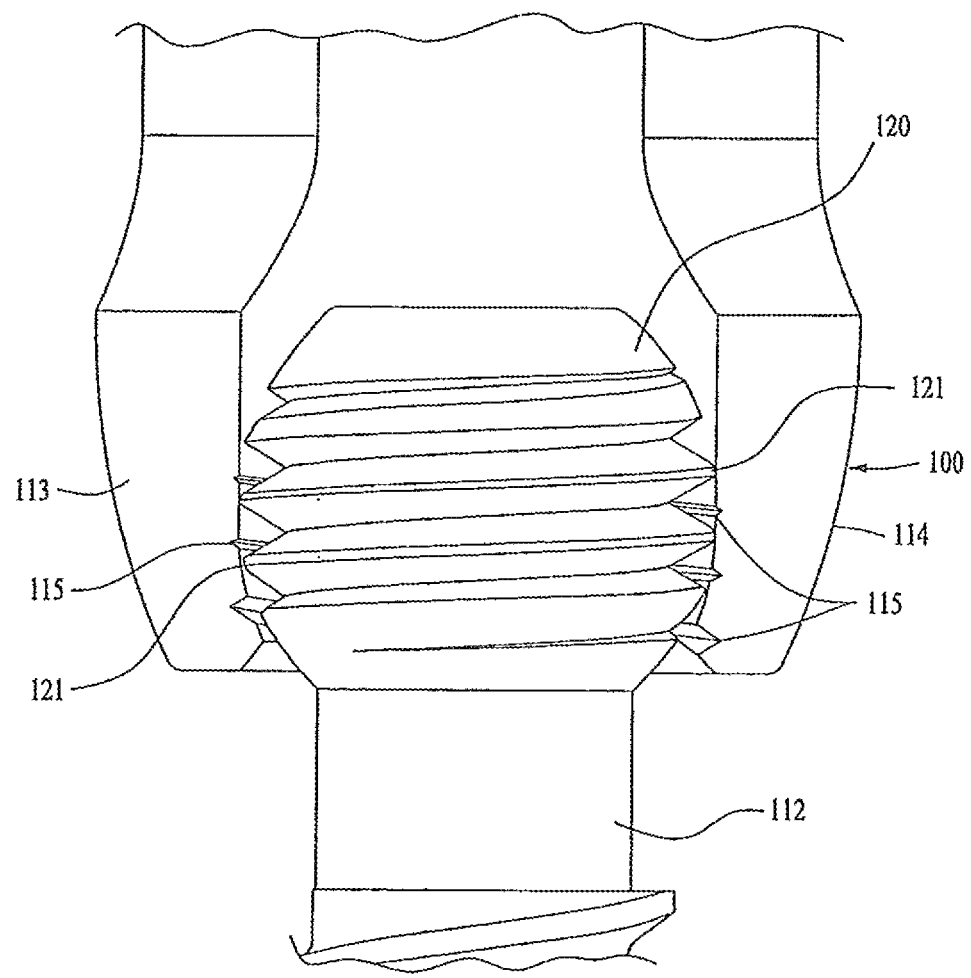
FIG. 11 is a perspective view of the modified pedicle screw and body member of FIG. 10 shown in the attached position prior to threading the body member over the screw head to form the mating relationship between the spherical lower portion of the screw head and the interior lower surface of the body member.

A modified form of the variable angle spinal screw assembly is illustrated in FIGS. 10 and 11. This modified form of the assembly enables the surgeon to insert the pedicle screw in the bone, by itself, unencumbered by the body member. In the prior embodiment, the pedicle screw 12 must be inserted through the body member 14 before the screw can be driven into the bone. With the body member attached, securement of the screw into the bone can be somewhat difficult. In the modified assembly 100, the outer surface of the spherical head portion 120 of the pedicle screw 112 is provided with threads 121, as seen in FIG. 10. As in the prior embodiment, the upper end of head portion 120 is provided with a vertical slot 122 used to drive the screw into place. The lower interior portion 113 of the body member 114 to be used with the modified pedicle screw 112 is provided with threads 115 adapted to engage threads 121 on the screw. As a result, the body member 114 can be threaded onto (see FIG. 11) and over the head 120 of the screw 112 after the screw is driven into place. With the exception of threads 121 and 115, the pedicle screw 112 and body member 114 are identical in configuration to the screw 12 and body member 14 of the prior embodiment. Thus, after the body member 114 is threaded onto and over the screw head and is disposed within the interior of the lower end of body member 114, as seen in FIG. 11, the variable angular relationship therebetween is formed as in the prior embodiment.

Figure 12:
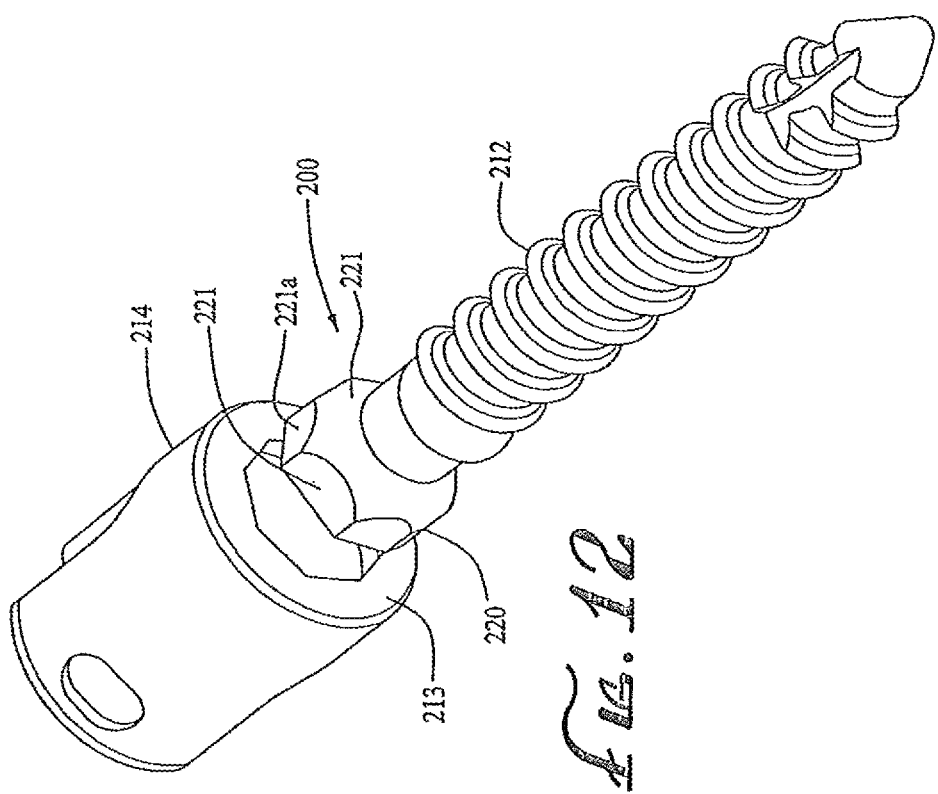
FIG. 12 is an exploded perspective view of another modified form of the pedicle screw and body member employed in the present invention.
Figure 13:
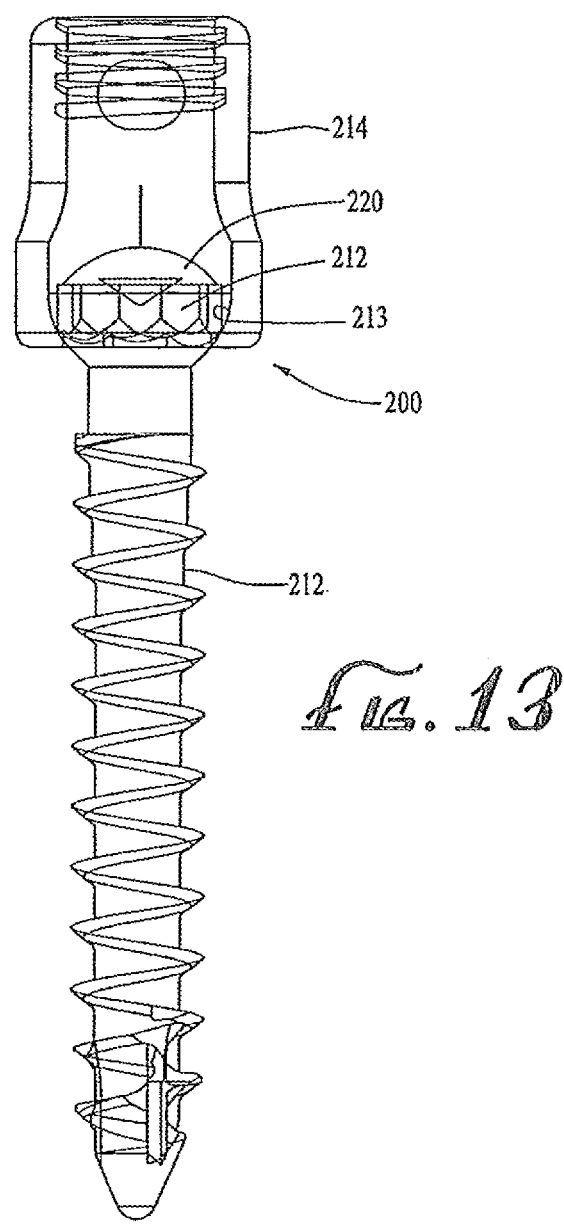
FIG. 13 is a representational side view of the embodiment of the pedicle screw and body member shown in FIG. 12 with the body member on the screw in the mating variable angle position.

A second modified form of the variable angle spinal screw assembly that enables the surgeon to insert the pedicle screw in the bone, by itself, unencumbered by the body member is illustrated in FIGS. 12 and 13. As seen therein, the mating threads on the pedicle screw 112 and body member 114 have been replaced with mating octagonal surfaces. In this second modified assembly 200, the outer surface of the spherical head portion 220 of the screw 212 is provided with an octagonal portion. The octagonal portion is comprised of eight contact surfaces 221, one of which (e.g. 221a) is unequal in length to the remaining surfaces. The lower interior portion 213 of the body member 214 to be used with the modified pedicle screw 212 is also provided with an octagonally configured portion adapted to engage and mate with the octagonal surfaces on the screw head. Because of the inclusion of a differently-sized surface on both the screw and body member, the pedicle screw 212 will only align with the body member 214 in only one position, i.e., where the shortened contact surface on the screw head is aligned with the correspondingly shortened surface in the lower interior of the body member. Accordingly, the pedicle screw 212 can again be inserted into the bone without being attached to the body member 214. After the screw 212 is driven into place, the body member 214 can be inserted over the screw head with the octagonal surfaces thereon aligned with the corresponding surfaces on the screw head. By pressing the screw body downwardly, it is completely inserted onto the screw head and the mating octagonal surfaces are moved out of engagement. Upon rotating the body member and pulling upwardly on the body member, such that the head is disposed within the interior of the lower end of body member 214 the variable angular relationship therebetween illustrated in FIG. 13 is formed as in the prior embodiments. It is to be understood that this form of the present invention is not limited to the use of mating octagonal surfaces. Any polygonal configuration could be employed on the screw head and body member wherein at least one of the mating surfaces on the screw head and on the body member is correspondingly off-sized or otherwise differently configured from the remaining surfaces on the screw head and body member.

In another embodiment of the invention, the bushing 16 is not employed. The opposed axial slots 32 in the side wall 34 of the body member of the assembly define a seat for the fixation rod 19. When the locking cap is pressed into the body member with the fixation rod extending thereacross, the planar bottom surface 54 of the central projection 52 again abuts the fixation rod and, in this instance, presses the rod against the upper end of the head of the pedicle screw. For such applications, the body member and pedicle screw would be sized such that the upper surface of the screw would project above the bottom of the seat defined by the axially opposed slots 32 so as to enable the rod to press against the screw and create a rigid, yet adjustable, securement between the body member and the pedicle screw. This embodiment can also be utilized with the modified forms of the pedicle screw 128 and body member 114 shown in FIGS. 10 and 11. In all of these embodiments, the components of the variable angle spinal screw assembly are preferably formed of titanium.

Figure 7:
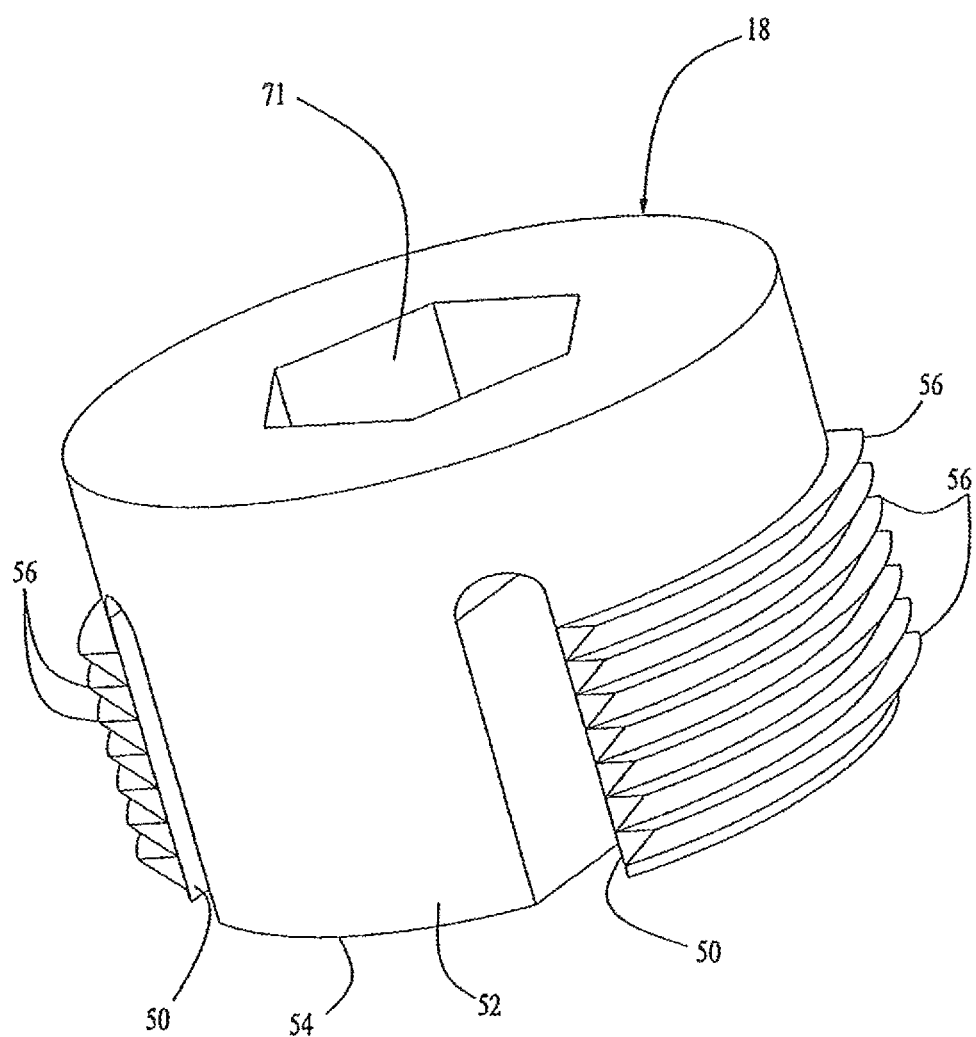
FIG. 7 is a second embodiment of the cap of the present invention.

It should be noted that while the preferred configuration of the locking cap provides a rounded and flush mounting on the upper ends of the body member 14 when the locking cap is fully inserted against the fixation rod, other locking cap configurations could be employed. For example, FIG. 7 illustrates a locking cap having a generally cylindrical perimeter portion in which the ratchet teeth 56 project radially therefrom along leg portions 50. This configuration is illustrated in FIG. 1. As a result, the upper end of the locking cap would be inwardly offset from the upper end of the body member without adversely effecting the operation of the variable angle spinal screw assembly. Various other changes and modifications also could be made in carrying out the present invention.

Although the present invention has been described by way of exemplary embodiments, it should be understood that many changes and substitutions may be made by those skilled in the art without departing from the spirit and the scope of the present invention, which is defined by the appended claims.

What is claimed and desired to be secured by Letters Patent is as follows:

1. A spinal screw assembly for securing a fixation rod to a bone, the spinal screw assembly comprising:
   a body member having a base defining an axial bore formed around a longitudinal axis with a lower opening in communication with a bottom of the body member, and a pair of arms extending upward from the base to define an open channel for receiving the fixation rod, the open channel being in communication with the axial bore, the axial bore including a rounded interior seating surface disposed about the lower opening and a non-threaded internal recess with a downwardly facing surface above the lower opening;
   a screw having a threaded shaft and a head disposed within the body member axial bore with the shaft extending downward through the lower opening, the screw head having a spherical outer surface with a single constant radius extending above and below a hemisphere plane to define an upper hemisphere and a lower hemisphere above and below the hemisphere plane, respectively, the spherical outer surface being slidably engagable with the axial bore rounded interior seating surface so as to allow variable angular movement of the screw relative to the body member during assembly; and a bushing snapped into the recess and having a portion with a slot in direct biased engagement with the screw head spherical outer surface, wherein the bushing provides a press fitment directly on the screw head so that the screw head spherical outer surface is held downwardly against the rounded interior seating surface in a frictional engagement to inhibit the screw and the body member from moving freely with respect to each other prior to the insertion and securement of the fixation rod with a closure to lock the assembly from any further variable angle movement.

2. The spinal screw assembly of claim 1, wherein the bushing is top loaded into the body member and resiliently snapped into the internal recess with the recess downwardly facing surface at least partially overlapping a top surface of the bushing to prevent the bushing from moving back up within the axial bore of the body member.

3. The spinal screw assembly of claim 1, wherein the slotted portion of the bushing extends from an outer surface to an inner surface of the bushing and further extends from a bottom surface of the bushing in a direction that is generally more vertical than horizontal with respect to a longitudinal center axis through the bushing.

4. The spinal screw assembly of claim 3, wherein the slotted portion of the bushing extends in a direction that is parallel with respect to the longitudinal center axis.

5. The spinal screw assembly of claim 1, wherein when the longitudinal axis of the body member and a longitudinal axis of the screw shaft are co-aligned, the bushing applies a downwardly directed pressure onto only the upper hemisphere of the screw head to bias the lower hemisphere of the screw head into the frictional engagement with the axial bore rounded interior seating surface, thereby inhibiting the screw and the body member from moving freely with respect to each other prior to the insertion and securement of the fixation rod with the closure.

6. The spinal screw assembly of claim 5, wherein the bushing is above and spaced apart from the lower hemisphere of the screw head.

7. The spinal screw assembly of claim 1, wherein the bushing is above and spaced from the axial bore rounded interior seating surface.

8. The spinal screw assembly of claim 1, wherein the bushing at least partially inhibits the screw head from moving upwards within the body member.

9. The spinal screw assembly of claim 1, wherein the screw is downloaded into the body member until the screw head slidably engages the axial bore rounded interior seating surface.

10. The spinal screw assembly of claim 1, wherein the bushing is configured to snap into the internal recess formed into the body member axial bore above the lower opening upon insertion into the axial bore to retain the bushing within the body member prior to the shank head being disposed within the axial bore.

11. The spinal screw assembly of claim 1, wherein the body member has a first of a projecting structure and a receiving aperture for the projecting structure, the bushing having a second of the projecting structure and the receiving aperture for the projecting structure, such that when the bushing is located within the body member axial bore, the projecting structure engages the receiving aperture to maintain proper alignment of the bushing with the body member.

12. The spinal screw assembly of claim 1, wherein the slotted portion of the bushing is positioned directly below the fixation rod.

13. The spinal screw assembly of claim 12, wherein the bushing further comprises a circular skirt having an upper portion with a pair of opposed interior concave wall surfaces formed therein to define a rod seat for engaging the fixation rod.

14. The spinal screw assembly of claim 13, wherein the pair of opposed interior concave wall surfaces defining the rod seat extend upwardly past a midpoint of the fixation rod and are slightly inwardly inclined to provide a holding force when the fixation rod is pushed into the rod seat.

15. The spinal screw assembly of claim 13, further comprising a locking cap that, when joined with the body member in a fully assembled configuration around the fixation rod, bears against the fixation rod which in turn bears against the rod seat of the bushing to apply pressure to the screw head and press the screw head against the rounded interior seating surface of the body member so as to fix an angular position of the screw relative to the body member.

16. The spinal screw assembly of claim 1, wherein the lower opening includes at least a partial thread formed therein.

17. The spinal screw assembly of claim 1, wherein the non-threaded internal recess further comprises a pair of opposed apertures.

18. The spinal screw assembly of claim 1, wherein the body member has a bottom surface that is at least partially sloped so as to be non-perpendicular with respect to the longitudinal axis to provide for increased angular movement in at least one direction for the screw relative to the body member.

19. The spinal screw assembly of claim 1, wherein the body member pair of arms have outwardly facing planar surfaces that are parallel with respect to each other and with respect to the longitudinal axis.

20. The spinal screw assembly of claim 1, wherein the closure further includes at least one loading flank surface perpendicular to the longitudinal axis of the body member and configured to lock the screw assembly.

21. The spinal screw assembly of claim 1, wherein the screw head has an internal tool engaging recess to screw the threaded shaft into the bone.

22. The spinal screw assembly of claim 1, wherein the closure includes a centrally disposed downwardly depending projecting structure that defines a planar bottom surface to compressively engage the fixation rod.

23. The spinal screw assembly of claim 22, wherein the centrally disposed downwardly depending projecting structure is integral with the closure.

24. The spinal screw assembly of claim 1, wherein after the bushing is snapped into the internal recess of the body member, the recess is configured to prevent the bushing from interfering with a locking function of the closure.

25. A spinal screw assembly for securing a fixation rod to a bone, the spinal screw assembly comprising:

a body member having a base defining an axial bore formed around a longitudinal axis with a lower opening in communication with a bottom of the body member, and a pair of arms extending upward from the base to define an open channel for receiving the fixation rod, the open channel being in communication with the axial bore, the axial bore including a rounded interior surface disposed about the lower opening and a non-threaded internal recess above the lower opening;

a screw having a threaded shaft and a head disposed within the body member axial bore with the shaft extending downward through the lower opening, the screw head having an at least partially spherical outer surface that is slidably engagable with the axial bore rounded interior surface so as to allow variable angular movement of the screw relative to the body member during assembly; and a biasing member disposed within the body member axial bore and having at least an outer surface portion positioned within the recess and a discontinuous inner surface portion in direct biased engagement with the screw head outer surface prior to the insertion and securement of the fixation rod with a closure, wherein the direct biased engagement provides a press fitment on the screw head that urges the screw head downwardly into a frictional engagement with the body member rounded interior surface and thereby inhibits the screw and the body member from moving freely with respect to each other prior to a locking of the assembly with the closure.

26. The spinal screw assembly of claim 25, wherein the biasing member discontinuous inner surface portion in direct biased engagement with the screw head at least partially spherical outer surface is further defined by a slot or gap.

27. The spinal screw assembly of claim 26, wherein the slot or gap extends from a biasing member inner surface to an outer surface and further extends from a bottom surface of the biasing member in a direction that is generally more vertical than horizontal with respect to a longitudinal center axis through the biasing member.

28. The spinal screw assembly of claim 25, wherein the biasing member is snapped into the internal recess.

29. The spinal screw assembly of claim 28, wherein the biasing member is snapped into the internal recess prior to the screw head being disposed within the body member axial bore.

30. The spinal screw assembly of claim 29, wherein the screw head is disposed within the body member axial bore through the lower opening.

* * * * *